US012774264B2

(12) United States Patent
Tessonnier et al.

(10) Patent No.: US 12,774,264 B2
(45) Date of Patent: Oct. 27, 2026

(54) ISOMERIZATION OF CYCLOHEXENEDICARBOXYLIC ACID AND ITS DERIVATIVES

(71) Applicant: IOWA STATE UNIVERSITY RESEARCH FOUNDATION, INC., Ames, IA (US)

(72) Inventors: Jean-Philippe Tessonnier, Ames, IA (US); Brent Howard Shanks, Ames, IA (US); Eric William Cochran, Ames, IA (US); Joseph Eugene Hadel, Ames, IA (US); Marco Nazareno Dell'anna, Ames, IA (US); Prerana Carter, Ames, IA (US)

(73) Assignee: IOWA STATE UNIVERSITY RESEARCH FOUNDATION, INC., Ames, IA (US)

( * ) Notice: Subject to any disclaimer, the term of this patent is extended or adjusted under 35 U.S.C. 154(b) by 582 days.

(21) Appl. No.: 18/027,492

(22) PCT Filed: Sep. 21, 2021

(86) PCT No.: PCT/US2021/051220
§ 371 (c)(1),
(2) Date: Mar. 21, 2023

(87) PCT Pub. No.: WO2022/061271
PCT Pub. Date: Mar. 24, 2022

(65) Prior Publication Data

US 2023/0373895 A1 Nov. 23, 2023

Related U.S. Application Data

(60) Provisional application No. 63/229,585, filed on Aug. 5, 2021, provisional application No. 63/080,964, filed on Sep. 21, 2020.

(51) Int. Cl.

| | |
|---|---|
| ***C07C 51/353*** | (2006.01) |
| ***C07C 61/24*** | (2006.01) |
| ***C08G 69/26*** | (2006.01) |
| ***C08G 69/28*** | (2006.01) |

(52) U.S. Cl.
CPC ............ *C07C 51/353* (2013.01); *C07C 61/24* (2013.01); *C08G 69/265* (2013.01); *C08G 69/28* (2013.01); *C07C 2601/16* (2017.05)

(58) Field of Classification Search
CPC ..... C07C 51/353; C07C 61/24; C08G 69/265; C08G 69/28
See application file for complete search history.

(56) References Cited

U.S. PATENT DOCUMENTS 2,498,533 A * 2/1950 Dimpfl ................. C08G 63/553 528/307
2,864,807 A 12/1958 Nobis et al.
3,240,759 A 3/1966 Crovatt, Jr. et al.
3,352,835 A 11/1967 Fritz et al.
3,483,105 A 12/1969 Gaetano
(Continued)

FOREIGN PATENT DOCUMENTS

CN 102660018 A 9/2012
CN 112646153 A 4/2021
(Continued)

OTHER PUBLICATIONS

International Preliminary Report on Patentability for PCT/US2021/051236 (Mar. 21, 2023).
(Continued)

*Primary Examiner* — Gregory Listvoyb
(74) *Attorney, Agent, or Firm* — Troutman Pepper Locke LLP (Rochester)

(57) ABSTRACT

The present application relates to a process for preparation of a compound of Formula (I): wherein $R^1$, $R^2$, and $R^3$ are as described herein and salts thereof and to a process of preparing such a compound. The present application also relates to a polymer of Formula (V): wherein $R^3$, Y, i, j, s, and m are as described herein and to a process for preparation of such polymers.

(I)

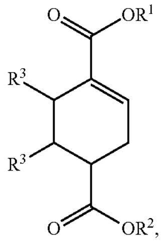

(V)

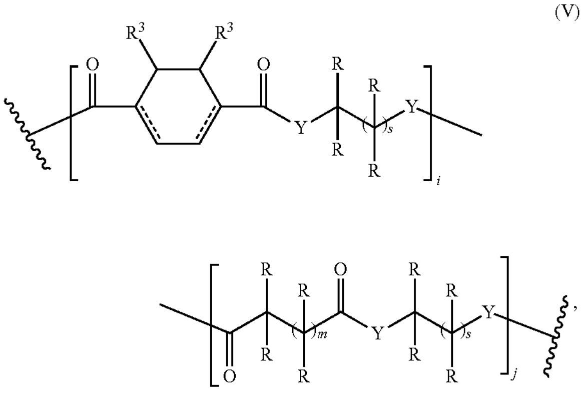

14 Claims, 9 Drawing Sheets

(56) References Cited

U.S. PATENT DOCUMENTS

| | | | | | |
|---|---|---|---|---|---|
| 3,558,547 | A | | 1/1971 | Kronstein | |
| 3,776,737 | A | * | 12/1973 | Williams | C08G 65/3324 430/908 |
| 3,776,980 | A | * | 12/1973 | Scardiglia | C08G 63/553 525/27 |
| 4,012,365 | A | | 3/1977 | Moriyama et al. | |
| 4,248,654 | A | | 2/1981 | Gude et al. | |
| 4,442,260 | A | | 4/1984 | Larsen | |
| 4,599,393 | A | | 7/1986 | Policastro | |
| 5,177,160 | A | | 1/1993 | Mukami et al. | |
| 5,663,290 | A | | 9/1997 | Heise et al. | |
| 5,919,441 | A | | 7/1999 | Mendolia et al. | |
| 5,981,680 | A | | 11/1999 | Petroff et al. | |
| 6,024,816 | A | | 2/2000 | Yamakawa et al. | |
| 6,620,362 | B1 | | 9/2003 | Jen | |
| 6,846,868 | B2 | | 1/2005 | Oka et al. | |
| 8,450,447 | B2 | | 5/2013 | Harris et al. | |
| 8,592,189 | B2 | | 11/2013 | Burgard et al. | |
| 10,633,750 | B2 | | 4/2020 | Tessonnier et al. | |
| 10,655,025 | B2 | | 5/2020 | Farrugua et al. | |
| 10,793,673 | B2 | | 10/2020 | Hernandez et al. | |
| 11,401,377 | B2 | | 8/2022 | Hernandez et al. | |
| 11,976,169 | B2 | | 5/2024 | Hernandez et al. | |
| 12,180,338 | B2 | | 12/2024 | Hernandez et al. | |
| 2010/0203275 | A1 | | 8/2010 | Hoffmann et al. | |
| 2010/0314243 | A1 | | 12/2010 | Frost et al. | |
| 2011/0052848 | A1 | | 3/2011 | Doshi et al. | |
| 2011/0189419 | A1 | | 8/2011 | Le et al. | |
| 2012/0301659 | A1 | | 11/2012 | Rao | |
| 2015/0376341 | A1 | | 12/2015 | Ait-Haddou et al. | |
| 2016/0017381 | A1 | | 1/2016 | Beckham et al. | |
| 2016/0347929 | A1 | | 12/2016 | Bendler et al. | |
| 2017/0129839 | A1 | | 5/2017 | Tessonnier et al. | |
| 2017/0130001 | A1 | | 5/2017 | Hernandez et al. | |
| 2019/0153156 | A1 | | 5/2019 | Matthiesen et al. | |
| 2019/0352521 | A1 | | 11/2019 | Farrugua et al. | |
| 2021/0024696 | A1 | | 1/2021 | Hernandez et al. | |
| 2022/0315700 | A1 | | 10/2022 | Hernandez et al. | |
| 2024/0076449 | A1 | | 3/2024 | Cochran et al. | |
| 2024/0254283 | A1 | | 8/2024 | Tessonnier et al. | |
| 2024/0343864 | A1 | | 10/2024 | Tessonnier et al. | |

FOREIGN PATENT DOCUMENTS

| | | | | | |
|---|---|---|---|---|---|
| DE | 19712248 | A1 | | 10/1998 | |
| EP | 0368690 | A1 | | 5/1990 | |
| EP | 0910599 | B1 | | 3/2004 | |
| EP | 2910600 | A1 | | 8/2015 | |
| EP | 3782976 | A1 | | 2/2021 | |
| JP | S61243045 | A | | 10/1986 | |
| JP | H06-18903 | B2 | | 3/1994 | |
| JP | H06248062 | A | | 9/1994 | |
| JP | 2003320618 | A | | 11/2003 | |
| WO | WO-2012082727 | A1 | * | 6/2012 | C08G 69/34 |
| WO | 2014/104483 | A1 | | 7/2014 | |
| WO | 2016/077361 | A1 | | 5/2016 | |
| WO | WO-2019099759 | A1 | * | 5/2019 | C08G 69/265 |
| WO | 2019/235559 | A1 | | 12/2019 | |
| WO | 2022/061275 | A1 | | 3/2022 | |

OTHER PUBLICATIONS

Capelli et al., "Bio-Adipic Acid Production by Catalysed Hydrogenation of Muconicacid in Mild Operating Conditions," Applied Catalysis B: Environmental 218:220-229 (2017).

Carter et al., "Bioenabled Platform to Access Polyamides with Built-In Target Properties," J. Am. Chem. Soc. 144:9548-9553 (2022).

International Search Report and Written Opinion for Application No. PCT/US18/61410 (mailed Mar. 22, 2019).

Hernandez et al., "Unsaturated Diacids for the Production of Bio-Enabled Nylon," NSF IIP Conference, POSTER, Atlanta, GA (Jun. 3, 2018).

International Search Report and Written Opinion for Application No. PCT/US21/51236 (mailed Feb. 17, 2022).

Tessonnier, "Unsaturated Diacids for the Production of Bio-Advantaged Nylon, " Presentation (2018).

Olson et al., "Amorphous Linear Aliphatic Polyesters for the Facile Preparation of Tunable Rapidly Degrading Elastomeric Devices and Delivery Vectors," J. Am. Chem. Soc. 128:13625-13633 (2006).

Olson et al., "Preparation of Unsaturated Linear Aliphatic Polyesters Using Condensation Polymerization," Micromol. 39:2808-2814 (2006).

Invitation to pay additional fees for Application No. PCT/US18/61410 (mailed Jan. 23, 2019).

Fredrickson et al., "Multicritical Phenomena and Microphase Ordering in Random Block Copolymer Melts," Macromolecules 25:6341-6354 (1992).

Suastegui et al. "Combining Metabolic Engineering and Electrocatalysis: Application to the Production of Polyamides from Sugar," Angew. Chem. Int. Ed. Engl. Communication 55(7):2368-2373 (2016).

Machine Translation of JP 2003320618 (Year: 2019).

Machine Translation of WO 201404483 (Year: 2019).

Cohran et al., "BRDI: Bioadvantaged Heterogeneous Polymers for Green Packaging Applications," Grant Proposal Mar. 27, 2015.

Matthiesen et al., "Electrochemical Conversion of Biologically Produced Muconic Acid: Key Considerations for Scale-Up and Corresponding Technoeconomic Analysis," ACS Sustainable Chem. Eng. 4:7098-7109 (2016).

Odian, Principles of Polymerization, 3rd Ed., Staten Island, NY: John Wiley & Sons, Inc, pp. 19-23 and 141-49 (1991).

Office Action for U.S. Appl. No. 16/192,937 (May 3, 2021).

Office Action for U.S. Appl. No. 16/192,937 (Nov. 10, 2020).

Office Action for U.S. Appl. No. 15/348,561 (Nov. 20, 2019).

Office Action for U.S. Appl. No. 15/348,561 (Mar. 22, 2019).

International Preliminary Report on Patentability for Application No. PCT/US18/61410 (May 19, 2020).

Hoyle et al., "Thiol-Ene Click Chemistry," Angew. Chem. Int. Ed. 49:1540-1573 (2010).

Office Action for U.S. Appl. No. 16/192,937 (Jan. 21, 2022).

Akiba et al., "Vulcanization and Crosslinking in Elastomers," Prog. Polym. Sci. 22:475-521 (1997).

Alibeik et al., The Effect of Thiolation on the Mechanical and Protein Adsorption Properties of Polyurethanes, European Polymer Journal 43:1415-1427 (2007).

Ates et al., "Side-Chain Functionalisation of Unsaturated Polyesters from Ring-Opening Polymerisation of Macrolactones by Thiol-Ene Click Chemistry," Polymer Chemistry 2:309-312 (2011).

Office Action for U.S. Appl. No. 17/004,613 (Dec. 9, 2021).

International Preliminary Report on Patentability for PCT/US2021/051220 (Mar. 21, 2023).

Office Action for U.S. Appl. No. 17/841,095 (Mar. 30, 2023).

Extended European Search Report for European Application No. 21870401.3 (Nov. 19, 2024).

Carraher et al., "Solvent-Driven Isomerization of cis, cis-Muconic Acid for the Production of Specialty and Performance-Advantaged Cyclic Biobased Monomers," Green Chemistry 22:6444-6454 (2020).

U.S. Appl. No. 18/027,480 to Tessonnier et al. filed on Mar. 21, 2023, first named inventor Jean-Philippe Tessonnier.

U.S. Appl. No. 18/357,269 to Cochran et al. filed on Jul. 24, 2023, first named inventor Eric William Cochran.

Yu, H. and G. A. Kraus, "Divergent Pathways to Isophthalates and Naphthalate Esters from Methyl Coumalate," Tetrahedron Letters 59:4008-4010 (2018).

International Search Report and Written Opinion for Corresponding Application No. PCT/US2021/051220 (Feb. 18, 2022).

"PubChem SID 369540629" [online database] [retrieved on Nov. 23, 2021] Retrieved from PubChem(https://pubchem.ncbi.nlm.nih.gov/substance/369540629) (May 25, 2018).

Office Action for U.S. Appl. No. 17/841,095 (Oct. 25, 2023).

International Search Report and Written Opinion for Application No. PCT/US2023/028434 (Dec. 19, 2023).

Invitation to Pay Additional Fees for Application No. PCT/US2023/028434 (mailed Oct. 27, 2023).

(56) References Cited

OTHER PUBLICATIONS

Karayannidis et al., "Synthesis, Crystallization and Tensile Properties of Poly(ethylene Terephthalate-co-2, 6-naphthalate)s with Low Naphthalate Units Content," Polymer 44:7801-7808 (2003).
Abdolmohammadi et al., "Analysis of the Amorphous and Interphase Influence of Comononomer Loading on Polymer Properties Towards Forwarding Bioadvantaged Copolyamides," Macromolecules 54(17):7910-7924 (2021).
U.S. Appl. No. 18/682,576 to Tessonnier et al. filed on Feb. 9, 2024, first named inventor Jean-Philippe Tessonnier.
Office Action for U.S. Appl. No. 18/357,269 (Apr. 17, 2026).
Office Action for U.S. Appl. No. 18/027,480 (Feb. 12, 2026).
Extended European Search Report for European Application No. 22856393.8 (Jun. 24, 2025).
Sakuta et al., "Production of Hexaric Acids from Biomass," International Journal of Molecular Sciences 20(3660): 1-20 (2019).
Ogata et al., "Copolycondensation of Hydroxyl Diesters and Active Diesters with Hexamethylenediamine," Journal of Polymer Science : Part A: Polymer Chemistry 15(6): 1523-1526 (1977).
Machine translation of JP S61243045 to Korori et al.
Office Action for U.S. Appl. No. 18/027,480, mailed Jul. 30, 2026.

* cited by examiner

ISOMERIZATION OF CYCLOHEXENEDICARBOXYLIC ACID AND ITS DERIVATIVES

This application is a national stage application under 35 U.S.C. § 371 of International Application No. PCT/US2021/051220, filed Sep. 21, 2021, which claims the priority benefit of U.S. Provisional Patent Application Ser. No. 63/229,585, filed Aug. 5, 2021, and U.S. Provisional Patent Application Ser. No. 63/080,964, filed Sep. 21, 2020, which are hereby incorporated by reference in their entirety.

This invention was made with government support under grant number DOE Contract No. DE-AC02-05CH11231 and DOE Grant No. DE-EE0008492 awarded by U.S. Department of Energy and under grant number NSF Grant No. CBET1804436 awarded by National Science Foundation. The government has certain rights in the invention.

FIELD

The present application relates to the isomerization of cyclohexenedicarboxylic acid and its derivatives.

BACKGROUND

Muconic acid (MA) can be converted into a variety of commodity chemicals and high value-added novel products (Shanks et al., "Bioprivileged Molecules: Creating Value From Biomass," *Green Chem.* 19(14):3177-3185 (2017); Khalil et al., "Muconic Acid Isomers as Platform Chemicals and Monomers in the Biobased Economy," *Green Chem.* 22(5):1517-1541 (2020)). cis,cis-Muconic acid (ccMA) is obtained primarily through glucose fermentation (Matthiesen et al., "Electrochemical Conversion of Muconic Acid to Biobased Diacid Monomers," *ACS Sustainable Chem. Eng.* 4(6):3575-3585 (2016)). ccMA can be first isomerized to the Diels-Alder active trans, trans isomer (ttMA) using U.S. Pat. No. 9,957,218 to Tessonnier et al. This molecule can then be reacted with ethylene to obtain an unsaturated cyclic diacid. These unsaturated MA derivatives, through the functionalization of their double bond, enable the synthesis of polyesters and polyamides with modified performance properties (Matthiesen et al., "Electrochemical Conversion of Biologically Produced Muconic Acid: Key Considerations for Scale-Up and Corresponding Technoeconomic Analysis," *ACS Sustainable Chem. Eng.* 4(12):7098-7109 (2016)). However, functionalization chemistry can be challenging depending on the position of this unsaturation.

Nylon-6,6 is a polyamide produced from the polycondensation reaction of adipic acid and hexamethylenediamine (HMDA) with a market share of US$20.5 billion in 2013 and US$40 billion by 2020 (Acmite Market Intelligence, "Market Report. Global Polyamide Market," 521 pp. (December 2014)). Nylon-6,6, a semicrystalline polymer, is used in numerous applications where high-temperature, solvent-proof, electrically-shielded parts are needed (Sabreen, S., "Adhesive Bonding of Polyamide (Nylon)," *Plastics Decorating* 2 pp. (2015)). However, nylon 6,6 suffers from some drawbacks that prevents it from being used even further—i.e. poor surface wettability and the hygroscopicity (nylon will absorb moisture>3%/mass of water from the atmosphere) (Sabreen, S., "Adhesive Bonding of Polyamide (Nylon)," *Plastics Decorating* 2 pp. (2015)).

The present application is directed to overcoming these and other deficiencies in the art.

SUMMARY

One aspect of the present application relates to a process for preparation of a compound of Formula (I):

(I)

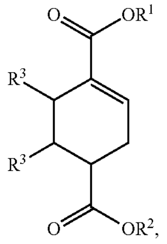

wherein $R^1$ is H or $C_{1-6}$ alkyl;

$R^2$ is H or $C_{1-6}$ alkyl; and each $R^3$ is independently selected from the group consisting of H, $C_{1-20}$ alkyl, aryl, carborane, heteroaryl, heterocyclyl, $C_{1-20}$ alkyl-O—Zn—O—$C_{1-20}$ alkyl, $C_{1-20}$ alkyl-O—Zn—O-heteroaryl, heteroaryl-O—Zn—O-heteroaryl, $C_{1-20}$ alkyl-O—Zn—O-heterocyclyl, heterocyclyl-O—Zn—O-heterocyclyl, heterocyclyl-O—Zn—O-heteroaryl, —$P(O)(R^6)_2$, —$P(O)(OR^5)_2$, —$C_{1-6}$ alkylene-$P(O)(R^6)_2$, and —$C_{1-6}$ alkylene-$P(O)(OR^5)_2$, wherein $C_{1-20}$ alkyl, heteroaryl, and heterocyclyl can be optionally substituted 1 to 3 times with $R^4$;

$R^4$ is selected from the group consisting of H, $C_{1-6}$ alkyl, SH, $NH_2$, $PH_2$, $P(O)(OR^5)_2$, $P(O)(OR^5)_3$, $P(O)(OR^5)_2R^6$, $P(O)(OR^5)(R^6)_2$, $P(O)(R^6)_2$, $BH_2$,

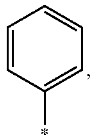, 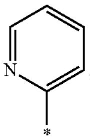, 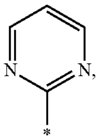 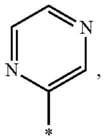, 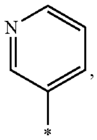,

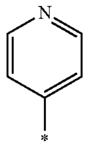, 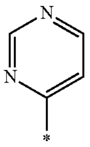 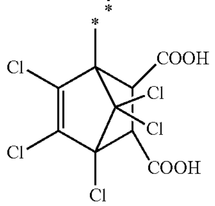,

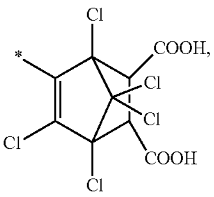 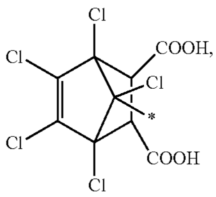

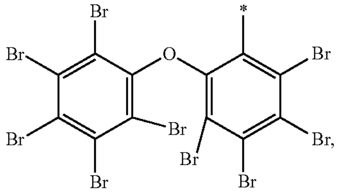

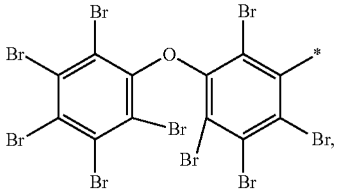

-continued

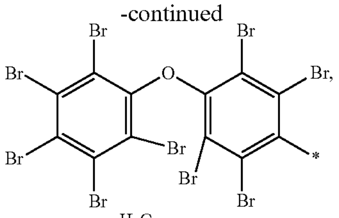

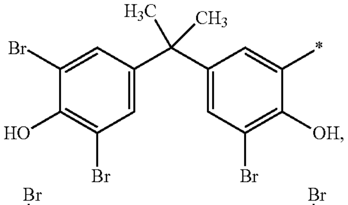

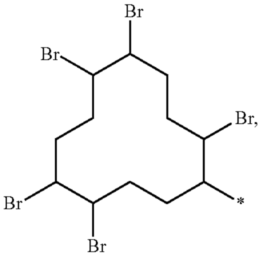

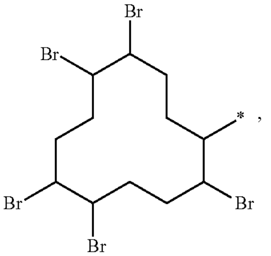

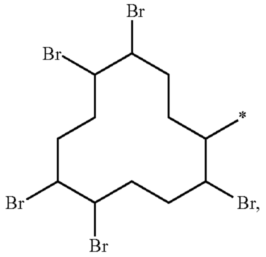

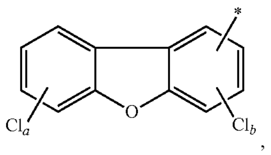

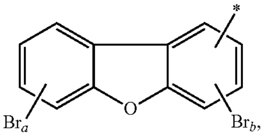

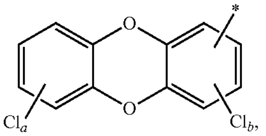

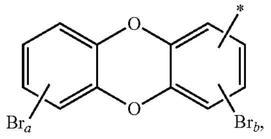

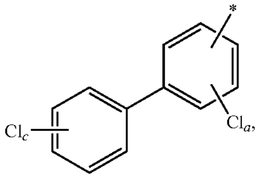 and 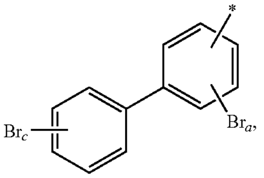

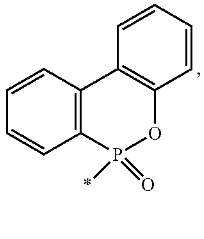, and 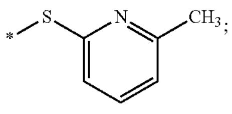;

a is 1, 2, 3, or 4;
b is 1, 2, or 3;
c is 1, 2, 3, 4, or 5;

each $R^5$ is independently selected from the group consisting of H, $C_{1-6}$ alkyl, $C_{1-6}$ alkenyl, and aryl, wherein aryl can be optionally substituted 1 to 3 times with halogen, or $C_{1-6}$ alkyl;

each $R^6$ is independently selected from the group consisting of H, $C_{1-6}$ alkyl, $C_{1-6}$ alkenyl, and aryl, wherein aryl can be optionally substituted 1 to 3 times with halogen, or $C_{1-6}$ alkyl,

 is the point of attachment of $R^4$ to $R^3$;

or a salt thereof.

This process includes:

providing a compound of Formula (II) having the structure:

(II)

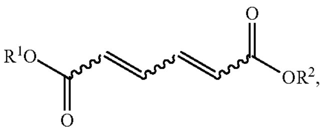

wherein the geometry around each double bond is independently either cis- or trans-, and forming the compound of Formula (I) from the compound of Formula (II).

Another aspect of the present application relates to compound of Formula (I):

(I)

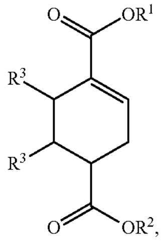

wherein $R^1$ is H or $C_{1-6}$ alkyl;

$R^2$ is H or $C_{1-6}$ alkyl; and each $R^3$ is independently selected from the group consisting of H, $C_{1-20}$ alkyl, aryl, carborane, heteroaryl, heterocyclyl, $C_{1-20}$ alkyl-O—Zn—O—$C_{1-20}$ alkyl, $C_{1-20}$ alkyl-O—Zn—O-heteroaryl, heteroaryl-O—Zn—O-heteroaryl, $C_{1-20}$ alkyl-O—Zn—O-heterocyclyl, heterocyclyl-O—Zn—O-heterocyclyl, heterocyclyl-O—Zn—O-heteroaryl, —$P(O)(R^6)_2$, —$P(O)(OR^5)_2$, —$C_{1-6}$ alkylene-$P(O)(R^6)_2$, and —$C_{1-6}$ alkylene-$P(O)(OR^5)_2$, wherein $C_{1-20}$ alkyl, heteroaryl, and heterocyclyl can be optionally substituted 1 to 3 times with $R^4$;

$R^4$ is selected from the group consisting of H, $C_{1-6}$ alkyl, SH, $NH_2$, $PH_2$, $P(O)(OR^5)_2$, $P(O)(OR^5)_3$, $P(O)(OR^5)_2R^6$, $P(O)(OR^5)(R^6)_2$, $P(O)(R^6)_2$, $BH_2$,

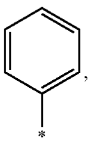, 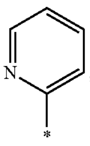, 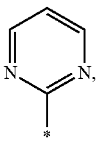, 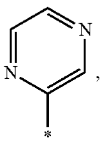, 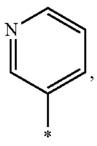,

-continued

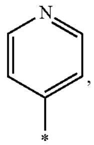,
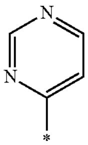,
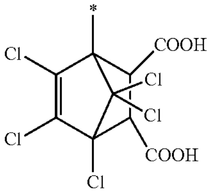,
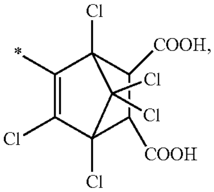
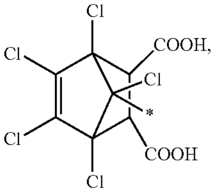
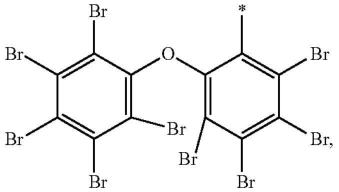
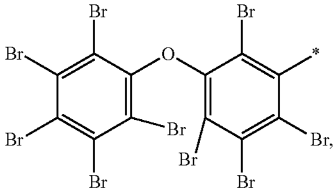
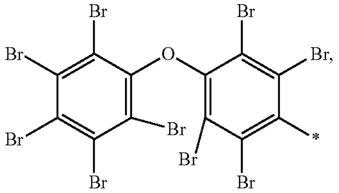
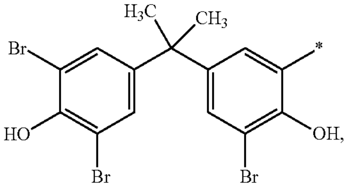
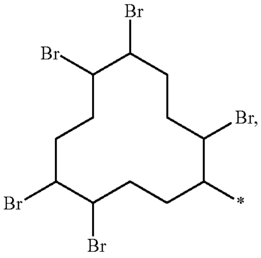
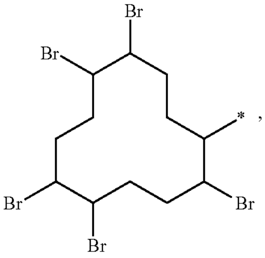, -continued

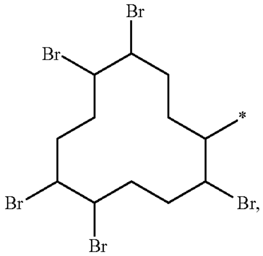
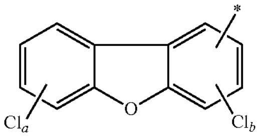,
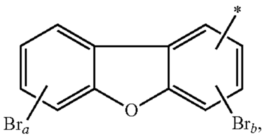
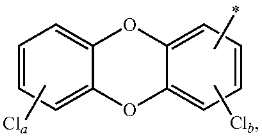
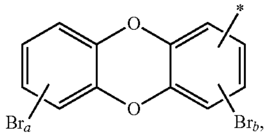
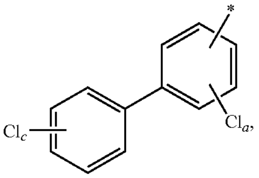
and
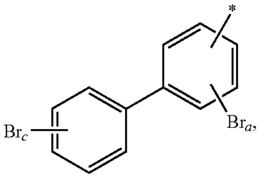
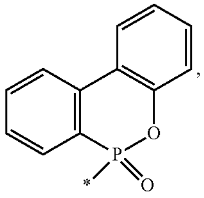,
and
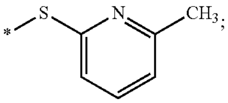

a is 1, 2, 3, or 4;

b is 1, 2, or 3;

c is 1, 2, 3, 4, or 5;

each $R^5$ is independently selected from the group consisting of H, $C_{1-6}$ alkyl, $C_{1-6}$ alkenyl, and aryl, wherein aryl can be optionally substituted 1 to 3 times with halogen, or $C_{1-6}$ alkyl;

each $R^6$ is independently selected from the group consisting of H, $C_{1-6}$ alkyl, $C_{1-6}$ alkenyl, and aryl, wherein aryl can be optionally substituted 1 to 3 times with halogen, or $C_{1-6}$ alkyl,

 is the point of attachment of $R^4$ to $R^3$;

or a salt thereof.

Another aspect of the present application relates to a process of making a polymer of Formula (V):

(V)

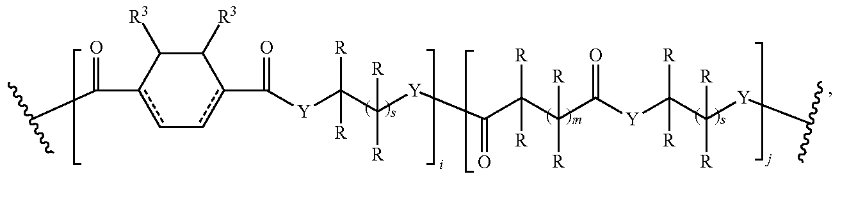

wherein

Y is NH or O;

R is independently selected from the group consisting of H and $C_{1-20}$ alkyl;

each $R^3$ is independently selected from the group consisting of H, $C_{1-20}$ alkyl, aryl, carborane, heteroaryl, heterocyclyl, $C_{1-20}$ alkyl-O—Zn—O—$C_{1-20}$ alkyl, $C_{1-20}$ alkyl-O—Zn—O-heteroaryl, heteroaryl-O—Zn—O-heteroaryl, $C_{1-20}$ alkyl-O—Zn—O-heterocyclyl, heterocyclyl-O—Zn—O-heterocyclyl, heterocyclyl-O—Zn—O-heteroaryl, —$P(O)(R^6)_2$, —$P(O)(OR^5)_2$, —$C_{1-6}$ alkylene-$P(O)(R^6)_2$, and —$C_{1-6}$ alkylene-$P(O)(OR^5)_2$, wherein $C_{1-20}$ alkyl, heteroaryl, and heterocyclyl can be optionally substituted 1 to 3 times with $R^4$;

$R^4$ is selected from the group consisting of H, $C_{1-6}$ alkyl, SH, $NH_2$, $PH_2$, $P(O)(OR^5)_2$, $P(O)(OR^5)_3$, $P(O)(OR^5)_2R^6$, $P(O)(OR^5)(R^6)_2$, $P(O)(R^6)_2$, $BH_2$,

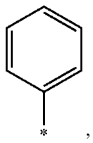
,
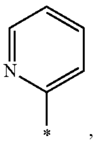
,
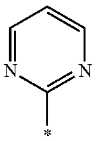
,
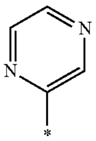
,
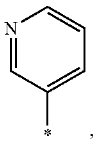
,
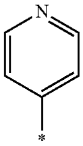
,
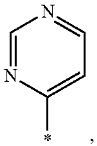
,
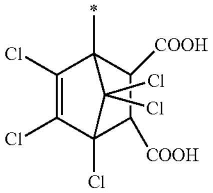
,
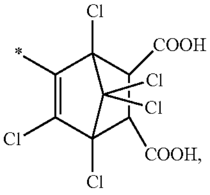
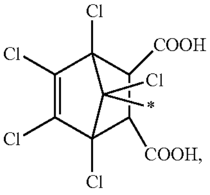
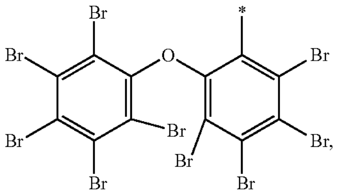
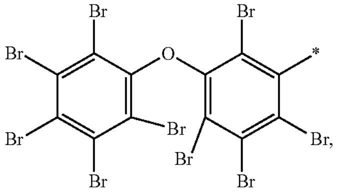
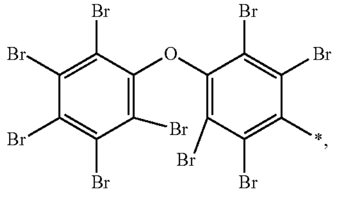

-continued

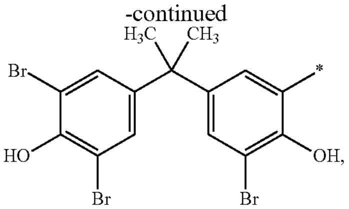
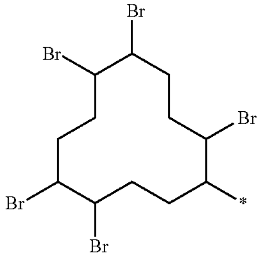
,
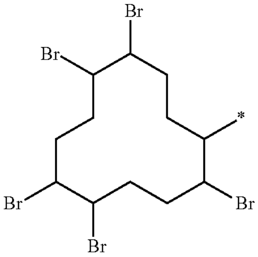
,
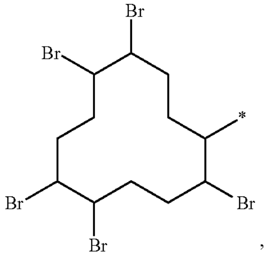
,
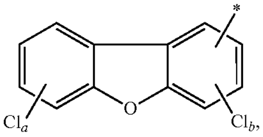
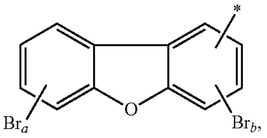
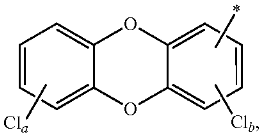
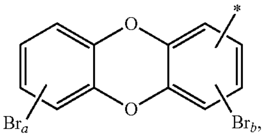
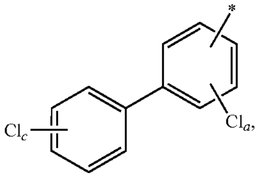
and
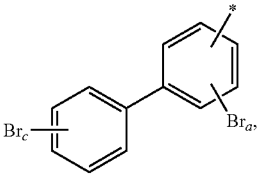
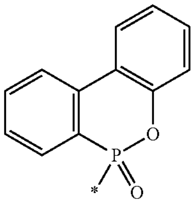
, and
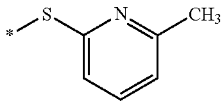
;

a is 1, 2, 3, or 4;

b is 1, 2, or 3;

c is 1, 2, 3, 4, or 5;

each $R^5$ is independently selected from the group consisting of H, $C_{1-6}$ alkyl, $C_{1-6}$ alkenyl, and aryl, wherein aryl can be optionally substituted 1 to 3 times with halogen, or $C_{1-6}$ alkyl;

each $R^6$ is independently selected from the group consisting of H, $C_{1-6}$ alkyl, $C_{1-6}$ alkenyl, and aryl, wherein aryl can be optionally substituted 1 to 3 times with halogen, or $C_{1-6}$ alkyl,

 is the point of attachment of $R^4$ to $R^3$;

i is 1 to 1,000,000;

j is 1 to 1,000,000;

m is 0 to 32;

s is 0 to 32; and

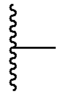

is a terminal group of the polymer;

is a single or a double bond, with only one  being a double bond.

This process includes:

providing a compound having the structure of Formula (I):

(I)

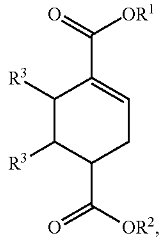

or a salt thereof, providing a compound having the structure of Formula (VI):

(VI)

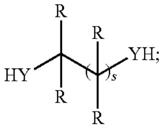

providing a compound having the structure of Formula (VII):

(VII)

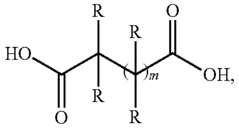

and reacting the compound of Formula (I), the compound of Formula (VI), and the compound of Formula (VII) under conditions effective to produce the polymer of Formula (V).

Another aspect of the present application relates to a polymer of Formula (V):

(V)

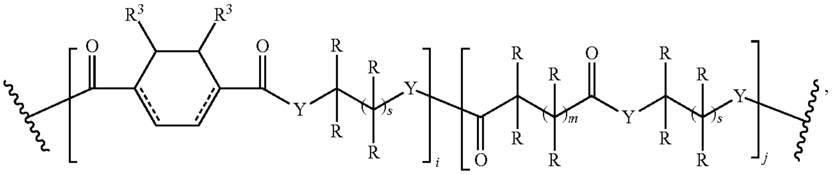

wherein

Y is NH or O;

R is independently selected from the group consisting of H and $C_{1-20}$ alkyl;

each $R^3$ is independently selected from the group consisting of H, $C_{1-20}$ alkyl, aryl, carborane, heteroaryl, heterocyclyl, $C_{1-20}$ alkyl-O—Zn—O—$C_{1-20}$ alkyl, $C_{1-20}$ alkyl-O—Zn—O-heteroaryl, heteroaryl-O—Zn—O-heteroaryl, $C_{1-20}$ alkyl-O—Zn—O-heterocyclyl, heterocyclyl-O—Zn—O-heterocyclyl, heterocyclyl-O—Zn—O-heteroaryl, —P(O)($R^6$)$_2$, —P(O)($OR^5$)$_2$, —$C_{1-6}$ alkylene-P(O)($R^6$)$_2$, and —$C_{1-6}$ alkylene-P(O)($OR^5$)$_2$, wherein $C_{1-20}$ alkyl, heteroaryl, and heterocyclyl can be optionally substituted 1 to 3 times with $R^4$;

$R^4$ is selected from the group consisting of H, $C_{1-6}$ alkyl, SH, $NH_2$, $PH_2$, P(O)($OR^5$)$_2$, P(O)$OR^5$)$_3$, P(O)($OR^5$)$_2R^6$, P(O)($OR^5$)($R^6$)$_2$, P(O)($R^6$)$_2$, $BH_2$,

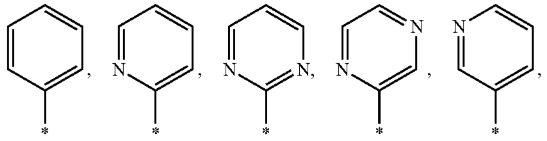

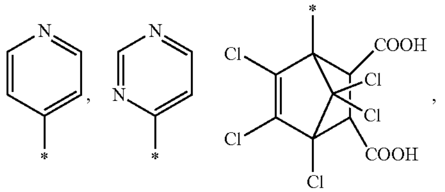

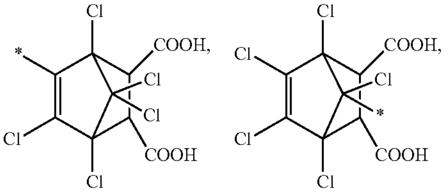

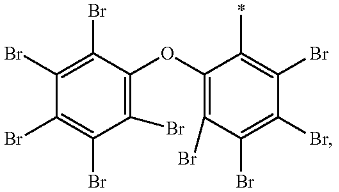

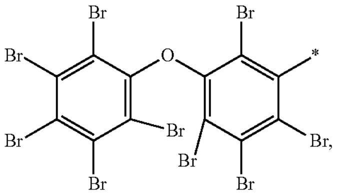

-continued

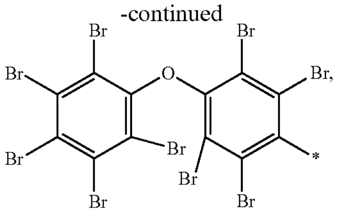

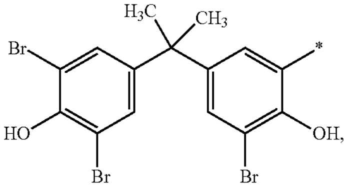

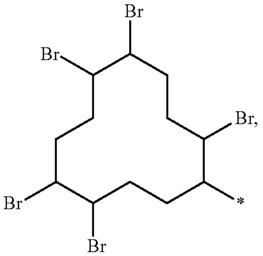

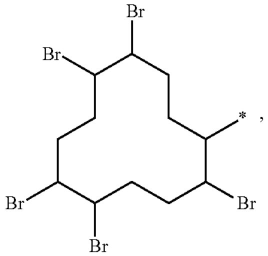

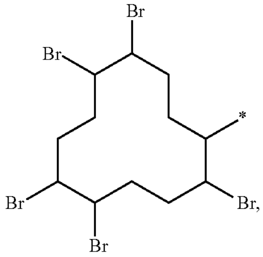

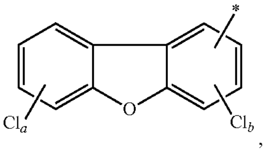

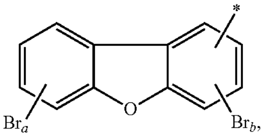

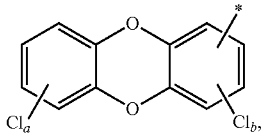

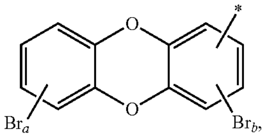

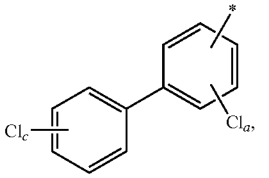

and

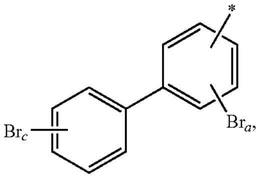

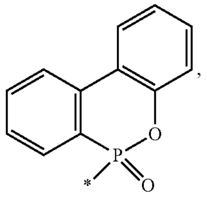

, and

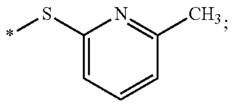

;

a is 1, 2, 3, or 4;

b is 1, 2, or 3;

c is 1, 2, 3, 4, or 5;

each $R^5$ is independently selected from the group consisting of H, $C_{1-6}$ alkyl, $C_{1-6}$ alkenyl, and aryl, wherein aryl can be optionally substituted 1 to 3 times with halogen, or $C_{1-6}$ alkyl;

each $R^6$ is independently selected from the group consisting of H, $C_{1-6}$ alkyl, $C_{1-6}$ alkenyl, and aryl, wherein aryl can be optionally substituted 1 to 3 times with halogen, or $C_{1-6}$ alkyl, $\overset{*}{\diagup}$ is the point of attachment of $R^4$ to $R^3$;

i is 1 to 1,000,000;

j is 1 to 1,000,000;

m is 0 to 32;

s is 0 to 32; and

is a terminal group of the polymer;

$\overline{- - -}$ is a single or a double bond, with only one of $\overline{- - -}$ being a double bond.

In conjunction with the present application, the isomerization of unsaturated cyclic derivatives of MA was studied. Trans,trans-muconic acid (ttMA) upon reaction with ethylene or any other dienophile (e.g., 1-octene) produced a cycloadduct with an unsaturation in the beta-gamma position. The position of this unsaturated group not only restricted chemistries available for functionalization, but also allowed for the possibility of retro Diels-Alder ring opening. However, by shifting the unsaturated group to the alpha-beta position the aforementioned complications were circumvented.

The present application demonstrates the potential of biobased molecules in synthesizing hydrophobic diacids for nylon-6,6. Nylon-6,6 provided an attractive candidate due to its application as a versatile engineering thermoplastic. This polyamide has excellent mechanical properties and high thermal stability due to its hydrogen bonding. As a result, it finds its application in a wide range of industries such as automotives, electronics, films and coatings. Despite its advantages, nylon-6,6 suffers from drawbacks such as high moisture uptake due to the amide linkages present in nylons, which absorb water through hydrogen bonding. The absorbed moisture acts as a plasticizer and alters the dimensional stability, negatively affecting physical and mechanical properties of the polymer. The current application demonstrates a synthesis technique utilizing Diels-Alder chemistry to react various vinyl-bearing groups with muconic acid-derivatives. Specifically, alpha olefins of different chain lengths (1-octene and 1-tetradecene) were reacted with dimethyl-trans,trans-muconate to synthesize hydrophobic cyclic diacids. These diacids were subsequently polymerized into a nylon-6,6 backbone and tested for property enhancements. The novel polyamides synthesized in this study decreased water uptake at 50% and 100% humidity by 3-folds compared to standard nylon-6,6. Contact angle measurements also showed a significant improvement.

DETAILED DESCRIPTION

Figure 1:
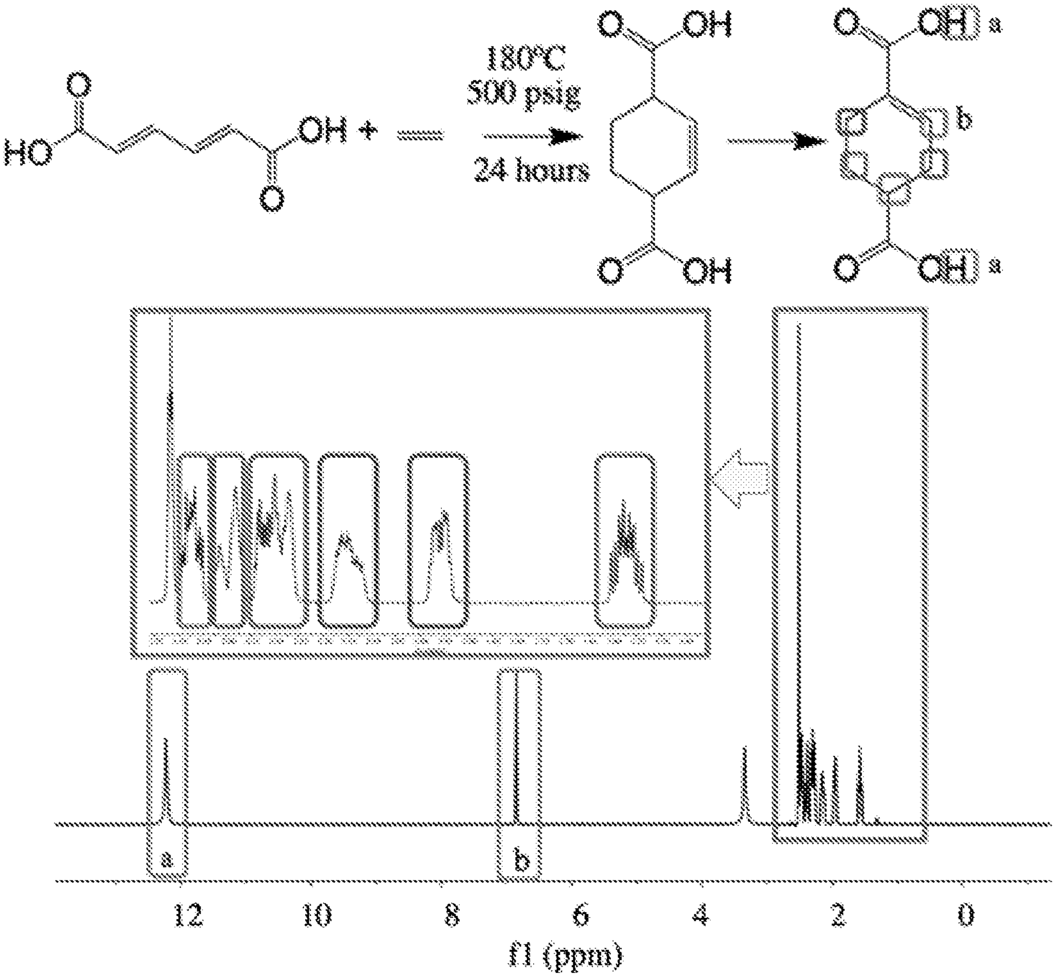
FIG. 1 is a $^1H$ NMR of Diels-Alder cycloaddition of trans,trans-muconic acid (ttMA) and ethylene in gamma-valerolactone.

One aspect of the present application relates to a process for preparation of a compound of Formula (I):

(I)

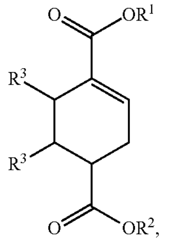

wherein $R^1$ is H or $C_{1-6}$ alkyl;

$R^2$ is H or $C_{1-6}$ alkyl; and each $R^3$ is independently selected from the group consisting of H, $C_{1-20}$ alkyl, aryl, carborane, heteroaryl, heterocyclyl, $C_{1-20}$ alkyl-O—Zn—O—$C_{1-20}$ alkyl, $C_{1-20}$ alkyl-O—Zn—O-heteroaryl, heteroaryl-O—Zn—O-heteroaryl, $C_{1-20}$ alkyl-O—Zn—O-heterocyclyl, heterocyclyl-O—Zn—O-heterocyclyl, heterocyclyl-O—Zn—O-heteroaryl, —$P(O)(R^6)_2$, —$P(O)(OR^5)_2$, —$C_{1-6}$ alkylene-$P(O)(R^6)_2$, and —$C_{1-6}$ alkylene-$P(O)(OR^5)_2$, wherein $C_{1-20}$ alkyl, heteroaryl, and heterocyclyl can be optionally substituted 1 to 3 times with $R^4$;

$R^4$ is selected from the group consisting of H, $C_{1-6}$ alkyl, SH, $NH_2$, $PH_2$, $P(O)(OR^5)_2$, $P(O)(OR^5)_3$, $P(O)(OR^5)_2R^6$, $P(O)(OR^5)(R^6)_2$, $P(O)(R^6)_2$, $BH_2$,

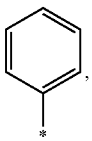, 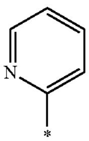, 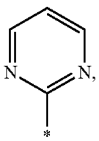, 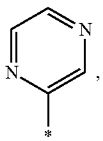, 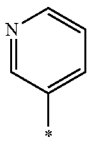,

-continued

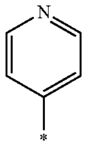, 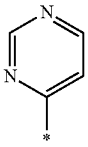 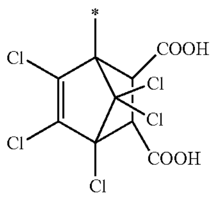,

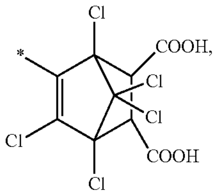 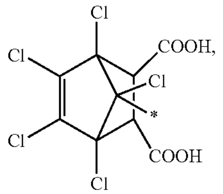

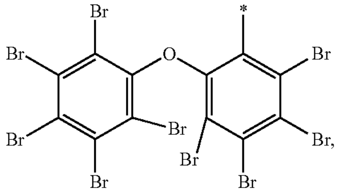

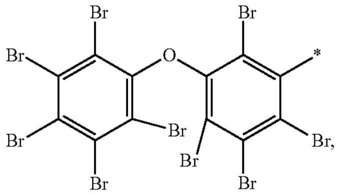

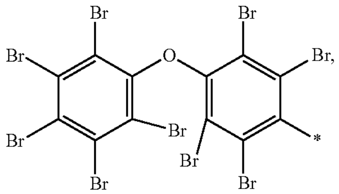

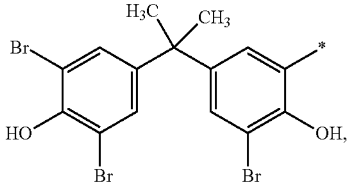

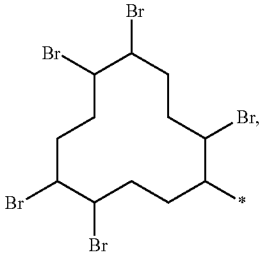 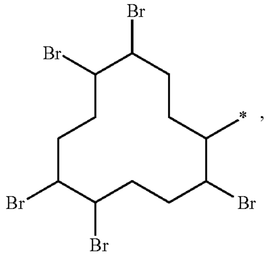 ,

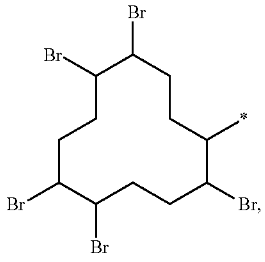 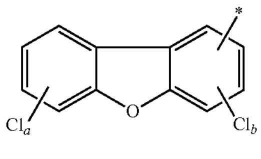 ,

-continued

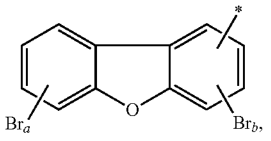,
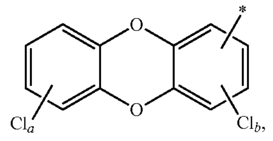,
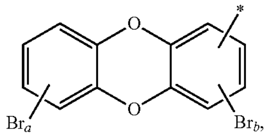,
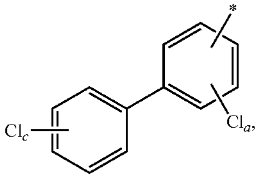, and 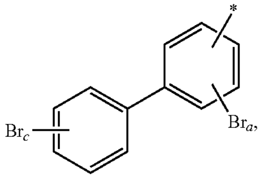,
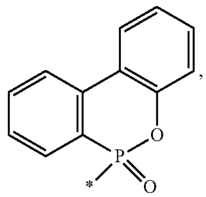, and 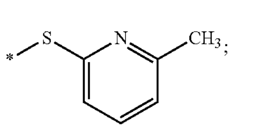;

a is 1, 2, 3, or 4;

b is 1, 2, or 3;

c is 1, 2, 3, 4, or 5;

each $R^5$ is independently selected from the group consisting of H, $C_{1-6}$ alkyl, $C_{1-6}$ alkenyl, and aryl, wherein aryl can be optionally substituted 1 to 3 times with halogen, or $C_{1-6}$ alkyl;

each $R^6$ is independently selected from the group consisting of H, $C_{1-6}$ alkyl, $C_{1-6}$ alkenyl, and aryl, wherein aryl can be optionally substituted 1 to 3 times with halogen, or $C_{1-6}$ alkyl,

 is the point of attachment of $R^4$ to $R^3$;

or a salt thereof.

This process includes:

providing a compound of Formula (II) having the structure:

(II)

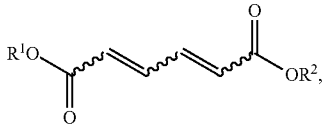

wherein the geometry around each double bond is independently either cis- or trans-, and forming the compound of Formula (I) from the compound of Formula (II).

As used above, and throughout the description herein, the following terms, unless otherwise indicated, shall be understood to have the following meanings. If not defined otherwise herein, all technical and scientific terms used herein have the same meaning as is commonly understood by one of ordinary skill in the art to which this technology belongs. In the event that there is a plurality of definitions for a term herein, those in this section prevail unless stated otherwise.

The term "alkyl" means an aliphatic hydrocarbon group which may be straight or branched having about 1 to about 20 carbon atoms in the chain. Branched means that one or more lower alkyl groups such as methyl, ethyl or propyl are attached to a linear alkyl chain. Exemplary alkyl groups include methyl, ethyl, n-propyl, i-propyl, n-butyl, t-butyl, n-pentyl, and 3-pentyl.

The term "alkylene" refers to a group obtained by removal of a hydrogen atom from an alkyl group. Non-limiting examples of alkylene include methylene and ethylene.

The term "alkenyl" means an aliphatic hydrocarbon group containing a carbon—carbon double bond and which may be straight or branched having about 2 to about 10 carbon atoms in the chain. Branched means that one or more lower alkyl groups such as methyl, ethyl, or propyl are attached to a linear alkenyl chain. Exemplary alkenyl groups include ethenyl, propenyl, n-butenyl, and i-butenyl.

The term "aryl" means an aromatic monocyclic or multicyclic ring system of 6 to about 14 carbon atoms, preferably of 6 to about 10 carbon atoms. Representative aryl groups include phenyl and naphthyl.

The term "organohalogen compounds" means organic compounds that contain at least one halogen bonded to carbon. The organohalogen compounds include but be not limited to chlorinated volatile organic compounds (CVOCs), trichloroethylene (TCE), perchloroethylene (PCE), dioxins, polybrominated dibenzo-p-dioxins (PBDD), polybrominated dibenzofurans (PBDF), polybromonated biphenyls (PBB), polychlorinated biphenyls (PCB), polychlorinated dibenzo-p-dioxins (PCDD), polychlorinated dibenzofurans (PCDF), and polychlorinated biphenyls. Suitable organohalogen compounds include chlorobenzene, bromobenzene, carbon tetrachloride, trichloroethane, dichloroethane, and benzyl chloride.

The term "halogen" means fluoro, chloro, bromo, or iodo.

The term "heteroaryl" means an aromatic monocyclic or multicyclic ring system of about 5 to about 14 ring atoms, preferably about 5 to about 10 ring atoms, in which one or more of the atoms in the ring system is/are element(s) other than carbon, for example, nitrogen, oxygen, or sulfur. In the case of multicyclic ring system, only one of the rings needs to be aromatic for the ring system to be defined as "Heteroaryl". Preferred heteroaryls contain about 5 to 6 ring atoms. The prefix aza, oxa, thia, or thio before heteroaryl means that at least a nitrogen, oxygen, or sulfur atom, respectively, is present as a ring atom. A nitrogen atom of a heteroaryl is optionally oxidized to the corresponding N-oxide. Representative heteroaryls include pyridyl, 2-oxo-pyridinyl, pyrimidinyl, pyridazinyl, pyrazinyl, triazinyl, furanyl, pyrrolyl, thiophenyl, pyrazolyl, imidazolyl, oxazolyl, isoxazolyl, thiazolyl, isothiazolyl, triazolyl, oxadiazolyl, thiadiazolyl, tetrazolyl, indolyl, isoindolyl, benzofuranyl, benzothiophenyl, indolinyl, 2-oxoindolinyl, dihydrobenzofuranyl, dihydrobenzothiophenyl, indazolyl, benzimidazolyl, benzooxazolyl, benzothiazolyl, benzoisoxazolyl, benzoisothiazolyl, benzotriazolyl, benzo[1,3]dioxolyl, quinolinyl, isoquinolinyl, quinazolinyl, cinnolinyl, pthalazinyl, quinoxalinyl, 2,3-dihydro-benzo[1,4]dioxinyl, benzo[1,2,3]triazinyl, benzo[1,2,4]triazinyl, 4H-chromenyl, indolizinyl, quinolizinyl, 6aH-thieno[2,3-d]imidazolyl, 1H-pyrrolo[2,3-b]pyridinyl, imidazo[1,2-a]pyridinyl, pyrazolo[1,5-a]pyridinyl, [1,2,4]triazolo[4,3-a]pyridinyl, [1,2,4]triazolo[1,5-a]pyridinyl, thieno[2,3-b]furanyl, thieno[2,3-b]pyridinyl, thieno[3,2-b]pyridinyl, furo[2,3-b]pyridinyl, furo[3,2-b]pyridinyl, thieno[3,2-d]pyrimidinyl, furo[3,2-d]pyrimidinyl, thieno[2,3-b]pyrazinyl, imidazo[1,2-a]pyrazinyl, 5,6,7,8-tetrahydroimidazo[1,2-a]pyrazinyl, 6,7-dihydro-4H-pyrazolo[5,1-c][1,4]oxazinyl, 2-oxo-2,3-dihydrobenzo[d]oxazolyl, 3,3-dimethyl-2-oxoindolinyl, 2-oxo-2,3-dihydro-1H-pyrrolo[2,3-b]pyridinyl, benzo[c][1,2,5]oxadiazolyl, benzo[c][1,2,5]thiadiazolyl, 3,4-dihydro-2H-benzo[b][1,4]oxazinyl, 5,6,7,8-tetrahydro-[1,2,4]triazolo[4,3-a]pyrazinyl, [1,2,4]triazolo[4,3-a]pyrazinyl, 3-oxo-[1,2,4]triazolo[4,3-a]pyridin-2(3H)-yl, and the like.

As used herein, "heterocyclyl" refers to a stable 3- to 18-membered ring (radical) which consists of carbon atoms and from one to five heteroatoms selected from the group consisting of nitrogen, oxygen, and sulfur. For purposes of this application, the heterocycle may be a monocyclic, or a polycyclic ring system, which may include fused, bridged, or spiro ring systems; and the nitrogen, carbon, or sulfur atoms in the heterocycle may be optionally oxidized; the nitrogen atom may be optionally quaternized; and the ring may be partially or fully saturated. Examples of such heterocycles include, without limitation, azepinyl, azocanyl, pyranyl dioxanyl, dithianyl, 1,3-dioxolanyl, tetrahydrofuryl, dihydropyrrolidinyl, decahydroisoquinolyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, 2-oxoazepinyl, oxazolidinyl, oxiranyl, piperidinyl, piperazinyl, 4-piperidonyl, pyrrolidinyl, pyrazolidinyl, thiazolidinyl, tetrahydropyranyl, thiamorpholinyl, thiamorpholinyl sulfoxide, and thiamorpholinyl sulfone. Further heterocycles and heteroaryls are described in Katritzky et al., eds., *Comprehensive Heterocyclic Chemistry: The Structure, Reactions, Synthesis and Use of Heterocyclic Compounds*, Vol. 1-8, Pergamon Press, N.Y. (1984), which is hereby incorporated by reference in its entirety.

The term "monocyclic" used herein indicates a molecular structure having one ring.

The term "polycyclic" or "multi-cyclic" used herein indicates a molecular structure having two or more rings, including, but not limited to, fused, bridged, or spiro rings.

The term "substituted" or "substitution" of an atom means that one or more hydrogen on the designated atom is replaced with a selection from the indicated group, provided that the designated atom's normal valency is not exceeded.

"Unsubstituted" atoms bear all of the hydrogen atoms dictated by their valency. When a substituent is keto (i.e., =0), then two hydrogens on the atom are replaced. Combinations of substituents and/or variables are permissible only if such combinations result in stable compounds; by "stable compound" or "stable structure" is meant a compound that is sufficiently robust to survive isolation to a useful degree of purity from a reaction mixture, and formulation into an efficacious therapeutic agent.

The term "optionally substituted" is used to indicate that a group may have a substituent at each substitutable atom of the group (including more than one substituent on a single atom), provided that the designated atom's normal valency is not exceeded and the identity of each substituent is independent of the others. Up to three H atoms in each residue are replaced with alkyl, halogen, haloalkyl, hydroxy, loweralkoxy, carboxy, carboalkoxy (also referred to as alkoxycarbonyl), carboxamido (also referred to as alkylaminocarbonyl), cyano, carbonyl, nitro, amino, alkylamino, dialkylamino, mercapto, alkylthio, sulfoxide, sulfone, acylamino, amidino, phenyl, benzyl, heteroaryl, phenoxy, benzyloxy, or heteroaryloxy. "Unsubstituted" atoms bear all of the hydrogen atoms dictated by their valency. When a substituent is keto (i.e., =0), then two hydrogens on the atom are replaced. Combinations of substituents and/or variables are permissible only if such combinations result in stable compounds; by "stable compound" or "stable structure" is meant a compound that is sufficiently robust to survive isolation to a useful degree of purity from a reaction mixture, and formulation into an efficacious therapeutic agent.

Compounds described herein may contain one or more asymmetric centers and may thus give rise to enantiomers, diastereomers, and other stereoisomeric forms. Each chiral center may be defined, in terms of absolute stereochemistry, as (R)- or (S)-. The present application is meant to include all such possible isomers, as well as mixtures thereof, including racemic and optically pure forms. Optically active (R)- and (S)-, (−)- and (+)-, or (D)- and (L)-isomers may be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers. Likewise, all tautomeric forms are also intended to be included.

The term "salts" means the inorganic, and organic base addition salts, of compounds of the present application. Suitable metal salts include the sodium, potassium, calcium, barium, zinc, magnesium, and aluminum salts.

The term "copolymer" refers to a polymer derived from more than one species of monomer.

The term "alternating copolymer" or "alternating polymer" refers to a copolymer consisting of two or more species of monomeric units that are arranged in an alternating sequence (in which every other building unit is different $(\text{-}M_1M_2\text{-})_n$.

The term "random copolymer" or "random polymer" refers to a copolymer in which there is no definite order for the sequence of the different building blocks $(\text{-}M_1M_2M_1M_1M_2M_1M_2M_2\text{-})$.

The term "statistical copolymer" or "statistical polymer" refers to a copolymer in which the sequential distribution of the monomeric units obeys known statistical laws.

The term "block copolymer" or "block polymer" refers to a macromolecule consisting of long sequences of different repeat units. Exemplary block polymers include, but are not limited to $A_nB_m$, $A_nB_mA_m$, $A_nB_mC_k$, or $A_nB_mC_kA_n$.

In one embodiment, the compound of Formula (II) has a structure of Formula (IIa):

(IIa)

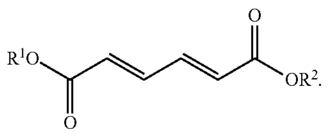

In another embodiment, the compound of Formula (I) is formed by reacting the compound of Formula (II) with a compound of Formula (III):

(III)

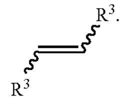

In another embodiment, the compound of Formula (I) is formed by reacting the compound of Formula (II) with a compound of Formula (III):

(III)

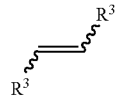

to form a compound of Formula (IV):

(IV)

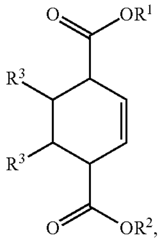

and converting the compound of Formula (IV) to the compound of Formula (I) in the presence of a base.

In one embodiment, the base can be selected from the group consisting of alkali hydroxides, primary amines, secondary amines, and tertiary amines.

In another embodiment, the base can be selected from the group consisting of potassium hydroxide, sodium hydroxide, dimethyl formamide, 1,4-diazabicyclo[2.2.2]octene, triethylamine, 1,8-diazabicyclo[5.4.0]undec-7-ene, 1,5-diazabicyclo[4.3.0]non-5-ene 4-dimethylaminopyridine, 1-methylimidazole, and 1,1,3,3-tetramethylguanidine.

In yet another embodiment, the compound of Formula (III) has the Formula (IIIa):

(IIIa)

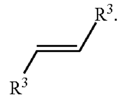

In a further embodiment, the compound of Formula (III) has the Formula (IIIb):

(IIIb)

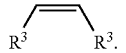

In another embodiment, the compound of Formula (I) has the Formula (Ia):

(Ia)

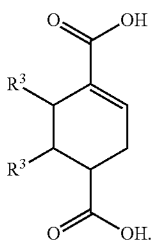

The compounds of the present application can be prepared according to the schemes described below. Initial Diels-Alder cycloaddition reaction between the compound of formula 1 and alkene 2 leads to formation of the compound of formula 3 (Scheme 1). This reaction can be carried out in a variety of solvents, for example in gamma-valerolactone, dichloromethane, toluene, water, dimethysulfoxide, dimethylformamide, acetonitrile, methanol, ethanol, or other such solvents or in a mixture of such solvents. This reaction can be carried out at room temperature or at elevated temperatures. For example, the reaction can be carried out at a temperature of 20° C. to 300° C., at a temperature of 100° C. to 250° C., or at a temperature of 100° C. to 200° C. The reaction can be carried out for 1 hour to 3 days, from 5 hours to 48 hours, from 12 hours to 24 hours. The reaction can be carried out in a regular reactor or in micro reactor. The reactor can be pressurized with nitrogen and ethylene. For example, the reactor can be pressurized with from 100 to 200 psig of nitrogen, from 110 to 190 psig of nitrogen, from 120 to 180 psig of nitrogen, from 130 to 170 psig of nitrogen, from 140 to 160 psig of nitrogen. Also for example, the reactor can be pressurized with from 400 to 600 psig of ethylene, from 425 to 575 psig of ethylene, from 450 to 550 psig of ethylene, from 475 to 525 psig of ethylene, from 490 to 510 psig of ethylene, and 500 psig of ethylene. The reaction can be carried out in the presence of a catalyst or without the catalyst. Suitable catalysts include $AlCl_3$, $FeCl_3$, holmium(III) trifluoromethanesulfonate, ytterbium(III) trifluoromethanesulfonate, (R)-3,3'-bis(2,4,6-triisopropylphenyl)-1,1'-binaphthyl-2,2'-diyl hydrogenphosphate, zeolites, and polyoxometalates Scheme 1.

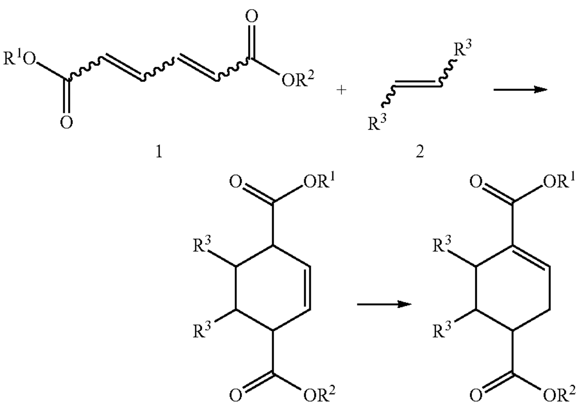

1 2 3 4

Compounds of formula 4 can be prepared by base catalyzed rearrangement of the compound of formula 3. The rearrangement step can be performed in a variety of solvents, for example in water, aqueous base solutions, and gamma-valerolactone. This reaction can be carried out at a temperature below room temperature, at room temperature, or at elevated temperatures. For example, this reaction can be carried out at temperature of 0° C. to 300° C., at a temperature of 25° C. to 275° C., at a temperature of 50° C. to 250° C., at a temperature of 75° C. to 225° C., at a temperature of 100° C. to 200° C., at a temperature of 125° C. to 225° C., at a temperature of 150° C. to 200° C., at a temperature of 20° C. to 100° C., or at a temperature 25° C. to 80° C.

Another aspect of the present application relates to compound of Formula (I):

(I)

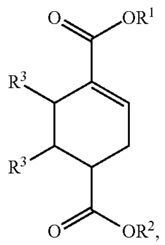

wherein $R^1$ is H or $C_{1-6}$ alkyl;

$R^2$ is H or $C_{1-6}$ alkyl; and each $R^3$ is independently selected from the group consisting of H, $C_{1-20}$ alkyl, aryl, carborane, heteroaryl, heterocyclyl, $C_{1-20}$ alkyl-O—Zn—O—$C_{1-20}$ alkyl, $C_{1-20}$ alkyl-O—Zn—O-heteroaryl, heteroaryl-O—Zn—O-heteroaryl, $C_{1-20}$ alkyl-O—Zn—O-heterocyclyl, heterocyclyl-O—Zn—O-heterocyclyl, heterocyclyl-O—Zn—O-heteroaryl, —$P(O)(R^6)_2$, —$P(O)(OR^5)_2$, —$C_{1-6}$ alkylene-$P(O)(R^6)_2$, and —$C_{1-6}$ alkylene-$P(O)(OR^5)_2$, wherein $C_{1-20}$ alkyl, heteroaryl, and heterocyclyl can be optionally substituted 1 to 3 times with $R^4$;

$R^4$ is selected from the group consisting of H, $C_{1-6}$ alkyl, SH, $NH_2$, $PH_2$, $P(O)(OR^5)_2$, $P(O)(OR^5)_3$, $P(O)(OR^5)_2R^6$, $P(O)(OR^5)(R^6)_2$, $P(O)(R^6)_2$, $BH_2$,

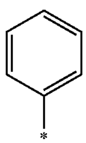 , 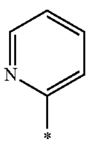 , 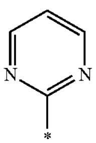 , 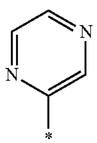 , 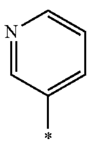 ,

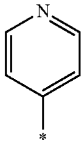 , 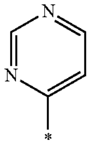 , 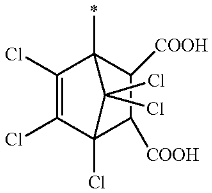 ,

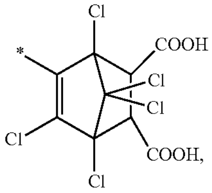

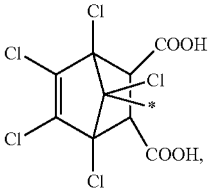

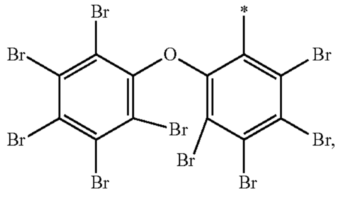

-continued

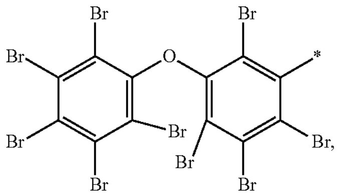

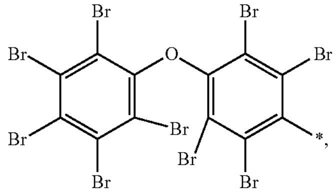

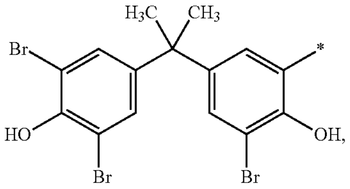

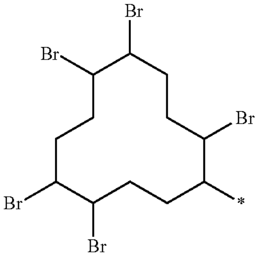 , 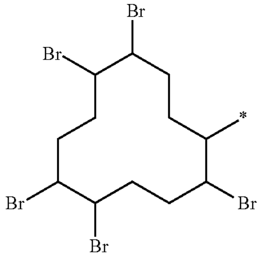 ,

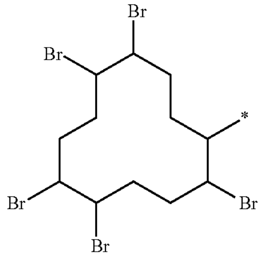 ,

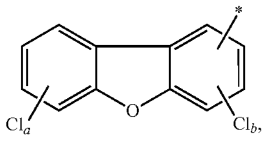

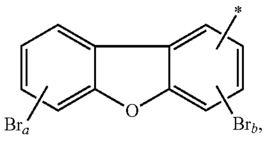

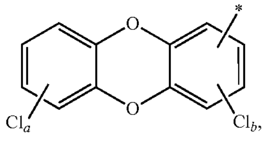

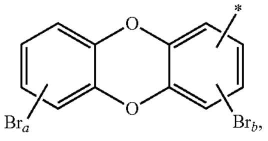

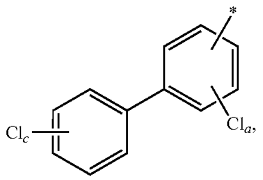 and 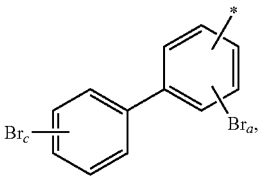

-continued

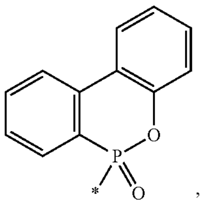

, and

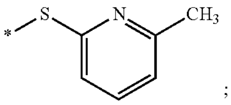

;

a is 1, 2, 3, or 4;
b is 1, 2, or 3;
c is 1, 2, 3, 4, or 5;
each $R^5$ is independently selected from the group consisting of H, $C_{1-6}$ alkyl, $C_{1-6}$ alkenyl, and aryl, wherein aryl can be optionally substituted 1 to 3 times with halogen, or $C_{1-6}$ alkyl;
each $R^6$ is independently selected from the group consisting of H, $C_{1-6}$ alkyl, $C_{1-6}$ alkenyl, and aryl, wherein aryl can be optionally substituted 1 to 3 times with halogen, or $C_{1-6}$ alkyl,
* is the point of attachment of $R^4$ to $R^3$;
or a salt thereof.

In one embodiment, $R^1$ in the compounds of Formula (I) is H or Me.

In another embodiment, $R^2$ in the compounds of Formula (I) is H or Me.

In yet another embodiment, $R^3$ in the compounds of Formula (I) is independently H, $C_6$ alkyl, or —P(O)(OH)$_2$.

In another embodiment, $R^3$ in the compounds of Formula (I) is independently H, $C_6$ alkyl, $C_{12}$ alkyl, or —P(O)(OH)$_2$.

In a further embodiment, the compound of Formula (I) has the formula

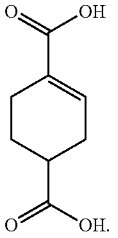 [SMILES: O=C(O)C1=CCC(C(=O)O)CC1]

In yet another embodiment, the compound of Formula (I) has the formula

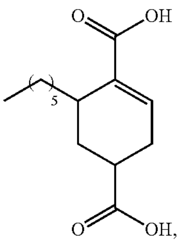

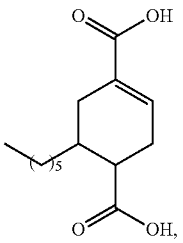

or the mixture thereof.

In yet another embodiment, the compound of Formula (I) has the formula

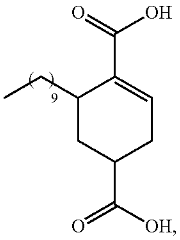

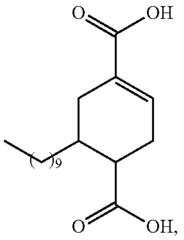

or the mixture thereof.

In a further embodiment, the compound of Formula (I) has the formula

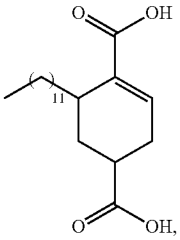

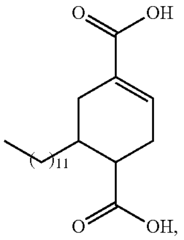

or the mixture thereof.

In yet another embodiment, the compound of Formula (I) has the formula

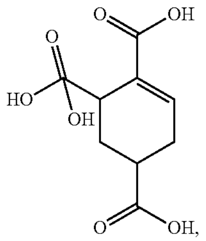

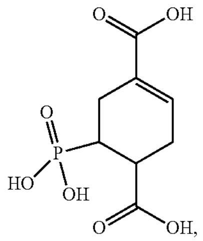

or the mixture thereof.

Another aspect of the present application relates to a process of making a polymer comprising the moiety:

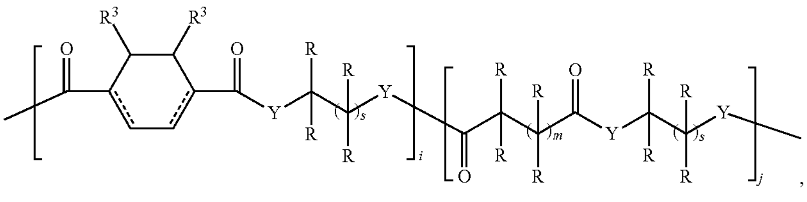

, wherein

Y is NH or O;

R is independently selected from the group consisting of H and $C_{1-20}$ alkyl;

each $R^3$ is independently selected from the group consisting of H, $C_{1-20}$ alkyl, aryl, carborane, heteroaryl, heterocyclyl, $C_{1-20}$ alkyl-O—Zn—O—$C_{1-20}$ alkyl, $C_{1-20}$ alkyl-O—Zn—O-heteroaryl, heteroaryl-O—Zn—O-heteroaryl, $C_{1-20}$ alkyl-O—Zn—O-heterocyclyl, heterocyclyl-O—Zn—O-heterocyclyl, heterocyclyl-O—Zn—O-heteroaryl, —$P(O)(R^6)_2$, —$P(O)(OR^5)_2$, —$C_{1-6}$ alkylene-$P(O)(R^6)_2$, and —$C_{1-6}$ alkylene-$P(O)(OR^5)_2$, wherein $C_{1-20}$ alkyl, heteroaryl, and heterocyclyl can be optionally substituted 1 to 3 times with $R^4$;

$R^4$ is selected from the group consisting of H, $C_{1-6}$ alkyl, SH, $NH_2$, $PH_2$, $P(O)(OR^5)_2$, $P(O)(OR^5)_3$, $P(O)(OR^5)_2R^6$, $P(O)(OR^5)(R^6)_2$, $P(O)(R^6)_2$, $BH_2$,

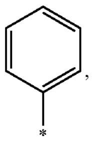, 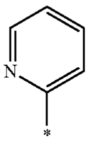, 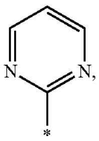, 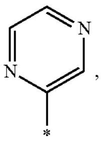, 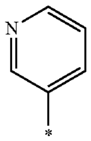,

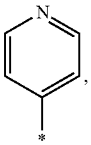, 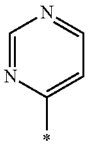, 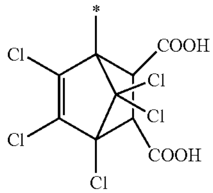,

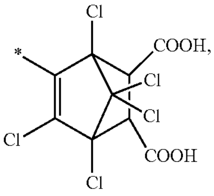 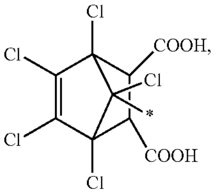

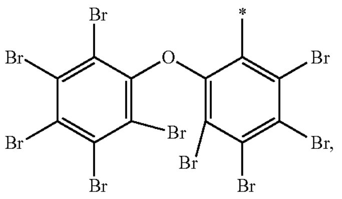

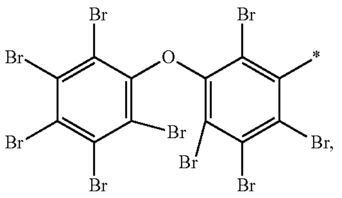

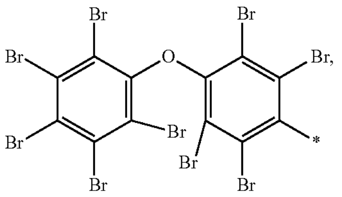

-continued

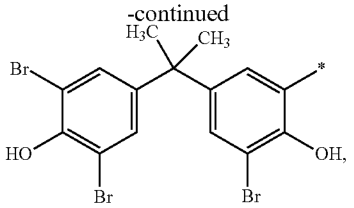

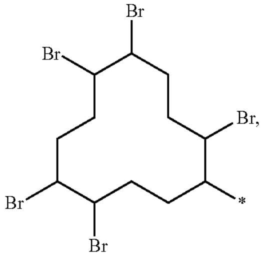 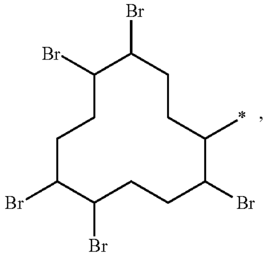,

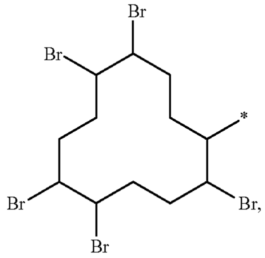 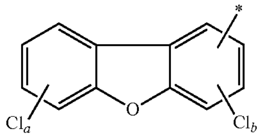,

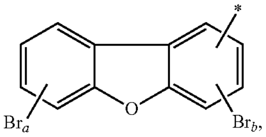 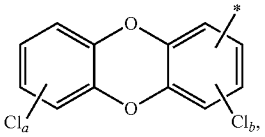

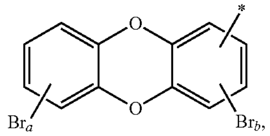

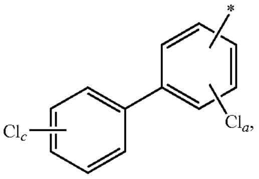 and 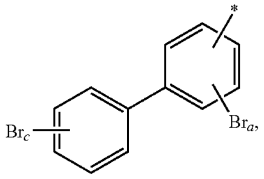

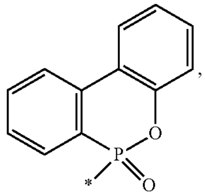, and 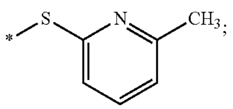

a is 1, 2, 3, or 4;

b is 1, 2, or 3;

c is 1, 2, 3, 4, or 5;

each $R^5$ is independently selected from the group consisting of H, $C_{1-6}$ alkyl, $C_{1-6}$ alkenyl, and aryl, wherein aryl can be optionally substituted 1 to 3 times with halogen, or $C_{1-6}$ alkyl;

each $R^6$ is independently selected from the group consisting of H, $C_{1-6}$ alkyl, $C_{1-6}$ alkenyl, and aryl, wherein aryl can be optionally substituted 1 to 3 times with halogen, or $C_{1-6}$ alkyl,

 is the point of attachment of $R^4$ to $R^3$;

i is 1 to 1,000,000;

j is 1 to 1,000,000;

m is 0 to 32;

s is 0 to 32; and

--- is a single or a double bond, with only one --- being a double bond.

This process includes:

providing a compound having the structure of Formula (I):

(I)

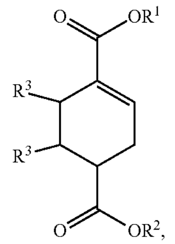

or a salt thereof, providing a compound having the structure of Formula (VI):

(VI)

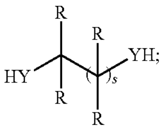

providing a compound having the structure of Formula (VII):

(VII)

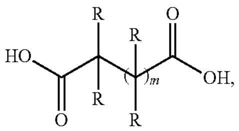

and reacting the compound of Formula (I), the compound of Formula (VI), and the compound of Formula (VII) under conditions effective to produce the polymer.

Another aspect of the present application relates to a process of making a polymer of Formula (V):

(V)

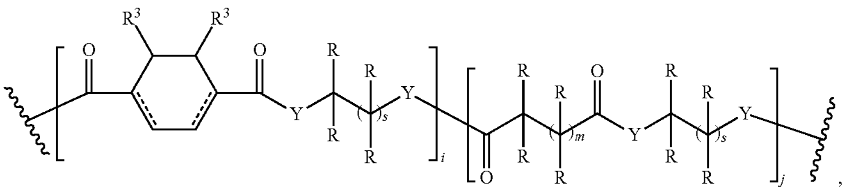

, wherein

Y is NH or O;

R is independently selected from the group consisting of H and $C_{1-20}$ alkyl;

each $R^3$ is independently selected from the group consisting of H, $C_{1-20}$ alkyl, aryl, carborane, heteroaryl, heterocyclyl, $C_{1-20}$ alkyl-O—Zn—O—$C_{1-20}$ alkyl, $C_{1-20}$ alkyl-O—Zn—O-heteroaryl, heteroaryl-O—Zn—O-heteroaryl, $C_{1-20}$ alkyl-O—Zn—O-heterocyclyl, heterocyclyl-O—Zn—O-heterocyclyl, heterocyclyl-O—Zn—O-heteroaryl, —$P(O)(R^6)_2$, —$P(O)(OR^5)_2$, —$C_{1-6}$ alkylene-$P(O)(R^6)_2$, and —$C_{1-6}$ alkylene-$P(O)(OR^5)_2$, wherein $C_{1-20}$ alkyl, heteroaryl, and heterocyclyl can be optionally substituted 1 to 3 times with $R^4$;

$R^4$ is selected from the group consisting of H, $C_{1-6}$ alkyl, SH, $NH_2$, $PH_2$, $P(O)(OR^5)_2$, $P(O)(OR^5)_3$, $P(O)(OR^5)_2R^6$, $P(O)(OR^5)(R^6)_2$, $P(O)(R^6)_2$, $BH_2$,

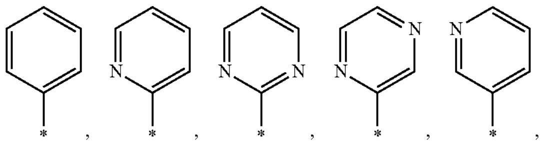

,

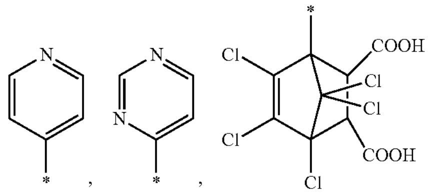

,

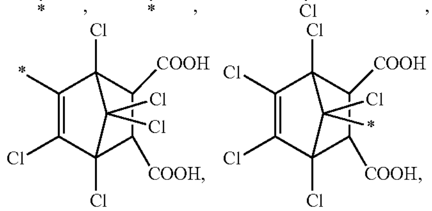

,

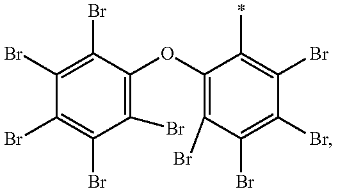

,

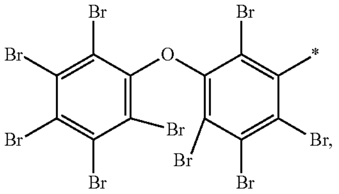

,

-continued

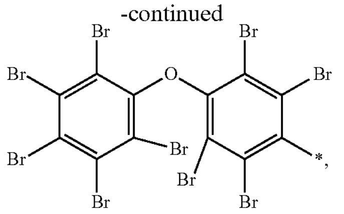

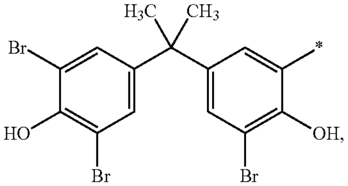

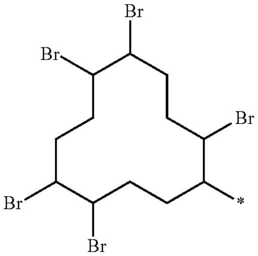 , 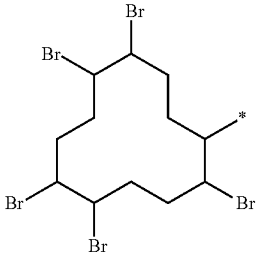 ,

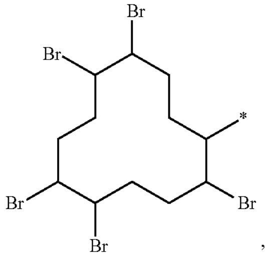 ,

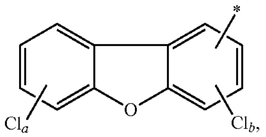 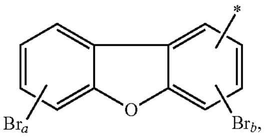

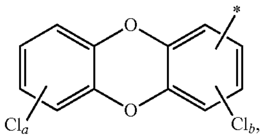 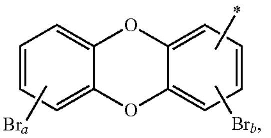

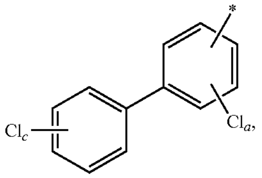 and 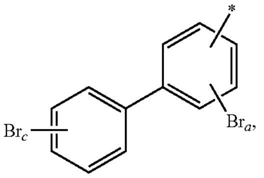

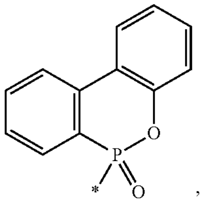 , and 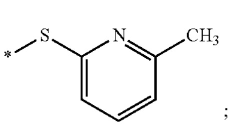 ;

a is 1, 2, 3, or 4;

b is 1, 2, or 3;

c is 1, 2, 3, 4, or 5;

each $R^5$ is independently selected from the group consisting of H, $C_{1-6}$ alkyl, $C_{1-6}$ alkenyl, and aryl, wherein aryl can be optionally substituted 1 to 3 times with halogen, or $C_{1-6}$ alkyl;

each $R^6$ is independently selected from the group consisting of H, $C_{1-6}$ alkyl, $C_{1-6}$ alkenyl, and aryl, wherein aryl can be optionally substituted 1 to 3 times with halogen, or $C_{1-6}$ alkyl,

 is the point of attachment of $R^4$ to $R^3$;

i is 1 to 1,000,000;

j is 1 to 1,000,000;

m is 0 to 32;

s is 0 to 32; and

is a terminal group of the polymer;

is a single or a double bond, with only one  being a double bond.

This process includes:

providing a compound having the structure of Formula (I):

(I)

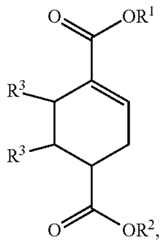

or a salt thereof, providing a compound having the structure of Formula (VI):

(VI)

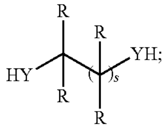

providing a compound having the structure of Formula (VII):

(VII)

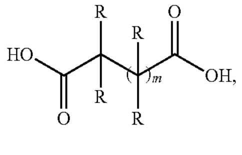

and reacting the compound of Formula (I), the compound of Formula (VI), and the compound of Formula (VII) under conditions effective to produce the polymer of Formula (V).

The polymers of the present application can be prepared according to the schemes described below. Polymers of formula 8 can be prepared by an initial polycondensation reaction (oligomer formation) between acids 5 and 6 and the compound of formula 7 followed by a polymerization step (polymer formation) (Schemes 2-4). The initial polycondensation reaction can be carried out neat or in a variety of solvents, for example in water, methanol (MeOH), ethanol (EtOH), isopropanol (i-PrOH), dimethylformamide (DMF), or other such solvents or in a mixture of such solvents. The initial polycondensation reaction (oligomer formation) can be carried out at a temperature of 100° C. to 300° C., at a temperature of 125° C. to 275° C., at a temperature of 150° C. to 250° C., at a temperature of 175° C. to 250° C., at a temperature of 200° C. to 250° C., or at a temperature of 200° C. to 240° C. The polymer formation step can be performed neat or in a variety of solvents, for example in phenols, cresols, hexafluoro-isopropanol, dimethylformamide (DMF) or other such solvents or in a mixture of such solvents. The final step in the polymerization (polymer formation) reaction can be carried out at a temperature of 100° C. to 400° C., at a temperature of 125° C. to 375° C., at a temperature of 150° C. to 350° C., at a temperature of 175° C. to 325° C., at a temperature of 200° C. to 300° C., at a temperature of 225° C. to 300° C., at a temperature of 250° C. to 300° C., or at a temperature of 260° C. to 300° C.

Scheme 2.

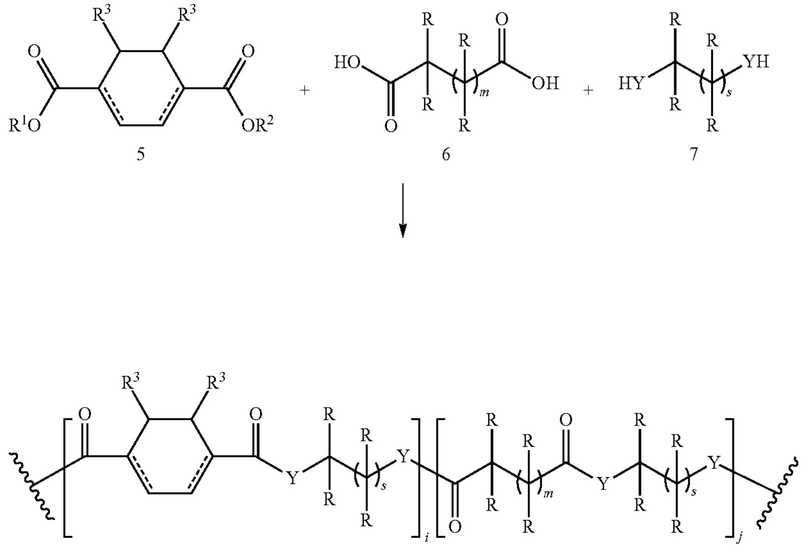

5 6 7

8

Scheme 3.

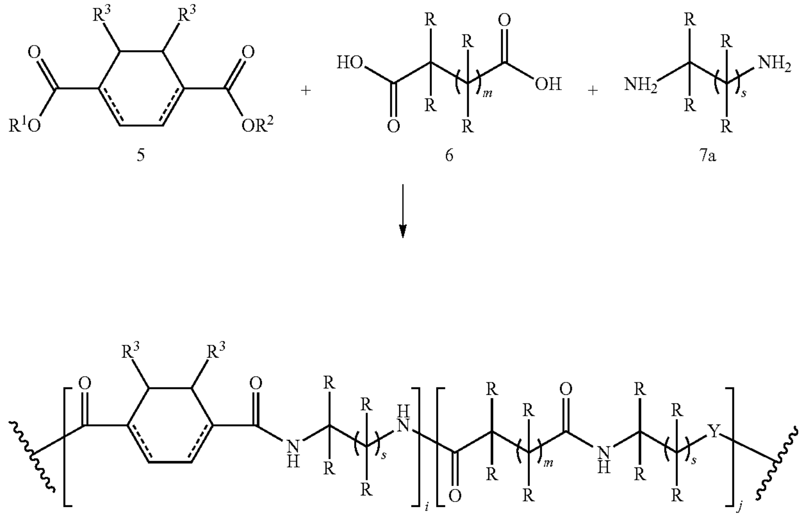

5 6 7a

8a

Scheme 4.

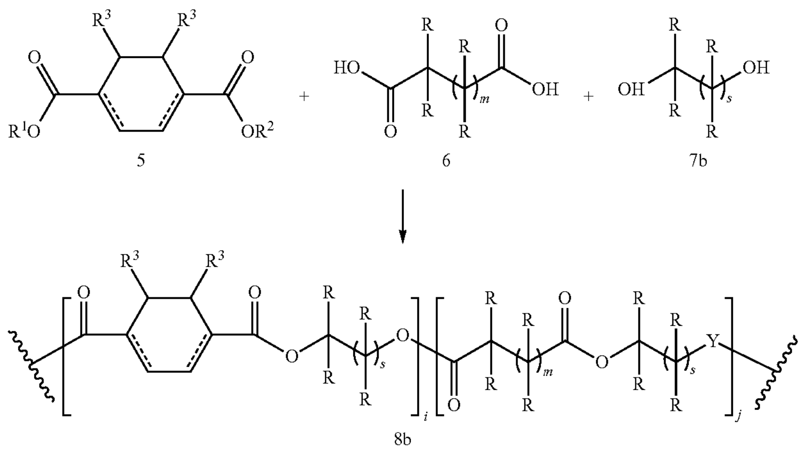

In some embodiments, polymers of formula 8 can be prepared by first preparing the salts between acid 5 and the compound of formula 7 (salt 1) and acid 6 and the compound of formula 7 (salt 2), followed by an initial polycondensation reaction (oligomer formation) and then a polymerization step. The salt formation can be carried out in a variety of solvents, for example in water, methanol (MeOH), ethanol (EtOH), isopropanol (i-PrOH), dimethylformamide (DMF), or other such solvents or in a mixture of such solvents. The salt formation can be carried out at a temperature of 20° C. to 100° C., at a temperature of 20° C. to 75° C., at a temperature of 20° C. to 50° C., at a temperature of 20° C. to 45° C., at a temperature of 20° C. to 40° C., at a temperature of 25° C. to 40° C., at a temperature of 30° C. to 40° C., at a temperature of 35° C. to 40° C., or at a temperature of 30° C. to 45° C. The salt formation can be carried out for 10 min to 24 hours, for 20 min to 20 hours, for 30 min to 18 hours, for 45 min to 12 hours, for 1 hour min to 6 hours, or for 1 hour min to 3 hours. The polycondensation reaction can be carried out neat or in a variety of solvents, for example in water, methanol (MeOH), ethanol (EtOH), isopropanol (i-PrOH), dimethylformamide (DMF), or other such solvents or in a mixture of such solvents. The initial polycondensation reaction can be carried out at a temperature of 100° C. to 300° C., at a temperature of 125° C. to 275° C., at a temperature of 150° C. to 250° C., at a temperature of 175° C. to 250° C., at a temperature of 200° C. to 250° C., or at a temperature of 200° C. to 240° C. The polymer formation step can be performed neat or in a variety of solvents, for example in phenols, cresols, hexafluoroisopropanol, dimethylformamide (DMF) or other such solvents or in a mixture of such solvents. The final step in the polymerization (polymer formation) reaction can be carried out at a temperature of 100° C. to 400° C., at a temperature of 125° C. to 375° C., at a temperature of 150° C. to 350° C., at a temperature of 175° C. to 325° C., at a temperature of 200° C. to 300° C., at a temperature of 225° C. to 300° C., at a temperature of 250° C. to 300° C., or at a temperature of 260° C. to 300° C.

Polycondensation reaction and polymer formation step can be performed in the same reaction vessel or different reaction vessels. In some embodiments, the reaction vessel was vented at least once during the process of polycondensation reaction and polymer formation step.

In some embodiments, polycondensation reaction and polymer formation step can be performed under inert atmosphere. For example, under nitrogen atmosphere or argon atmosphere.

In some embodiments, polycondensation reaction and polymer formation step can be performed under pressure. For example, polycondensation reaction and polymer formation step can be performed at a pressure of the inert gas from 50 psig to 300 psig, from 75 psig to 250 psig, from 100 psig to 200 psig, or from 125 psig to 200 psig, In other embodiments, polycondensation reaction and polymer formation step can be performed under atmospheric pressure.

During the process of making a polymer of Formula (V), salt 1 and salt 2 can be used in any amount from 1 to 99%. In some embodiments, salt 1 and salt 2 are mixed at the ratio of 5% of salt 1 and 95% of salt 2, 10% of salt 1 and 90% of salt 2, 15% of salt 1 and 85% of salt 2, 20% of salt 1 and 80% of salt 2, 25% of salt 1 and 75% of salt 2, 30% of salt 1 and 70% of salt 2, 35% of salt 1 and 65% of salt 2, 40% of salt 1 and 60% of salt 2, 45% of salt 1 and 55% of salt 2, 50% of salt 1 and 50% of salt 2, 55% of salt 1 and 45% of salt 2, 60% of salt 1 and 40% of salt 2, 65% of salt 1 and 35% of salt 2, 70% of salt 1 and 30% of salt 2, 75% of salt 1 and 25% of salt 2, 80% of salt 1 and 20% of salt 2, 85% of salt 1 and 15% of salt 2, 90% of salt 1 and 10% of salt 2, or 95% of salt 1 and 5% of salt 2.

In one embodiment, the compound of Formula (I) has the Formula (Ia):

(Ia)

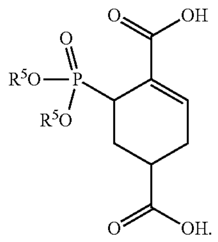

In another embodiment, the compound of Formula (Ia) has the Formula

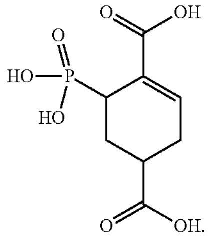 [SMILES: O=C(O)C1=CCC(C(=O)O)CC1P(=O)(O)O]

The repeating groups in the polymer of Formula (V) can be the same or different.

In another embodiment, the polymer of Formula (V) has the structure of Formula (Va):

(Va)

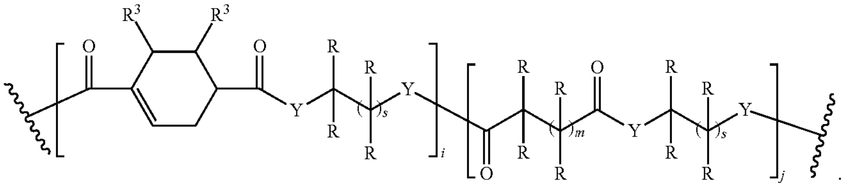

In yet another embodiment, the polymer of Formula (V) has the structure of Formula (Vb):

(Vb)

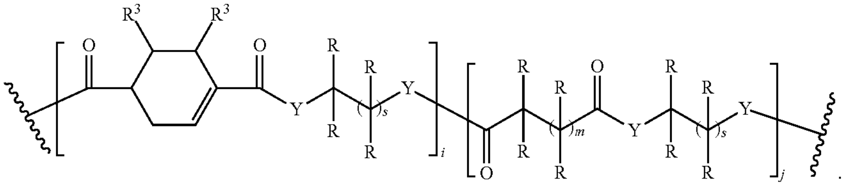

In a further embodiment, the polymer of Formula (V) has the structure of Formula (Vc):

(Vc)

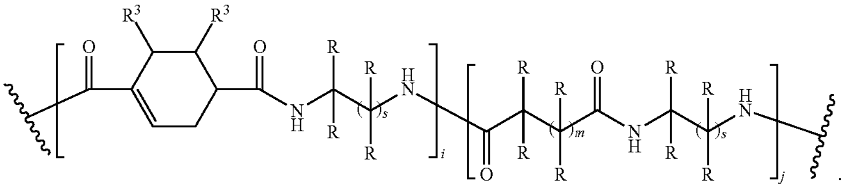

In yet another embodiment, the polymer of Formula (V) has the structure of Formula (Vd):

(Vd)

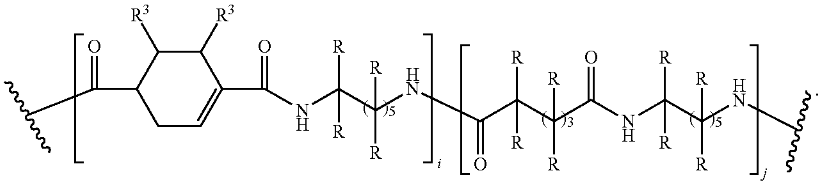

In another embodiment, the polymer of Formula (V) has the structure of Formula (Ve):

(Ve)

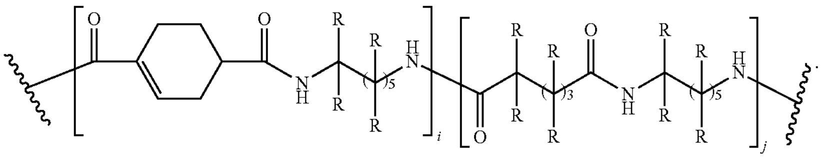

In yet another embodiment, the polymer of Formula (V) has the structure of Formula (Vf):

(Vf)

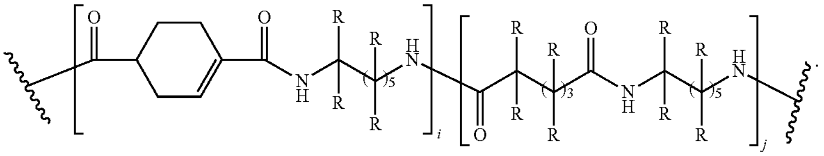

In a further embodiment, the polymer of Formula (V) has the structure of Formula (Vi):

(Vi)

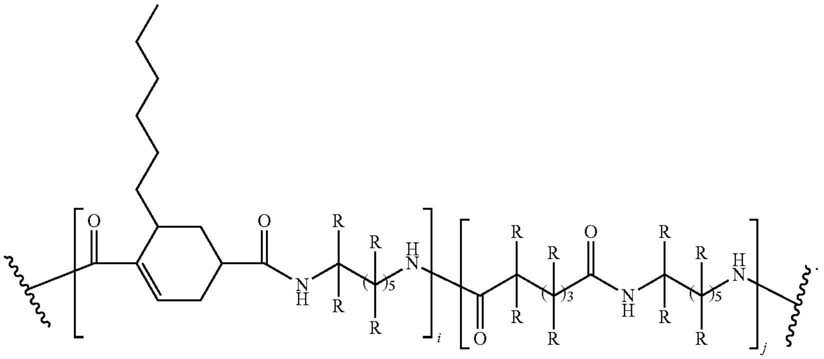

In yet another embodiment, the polymer of Formula (V) has the structure of Formula (Vj):

(Vj)

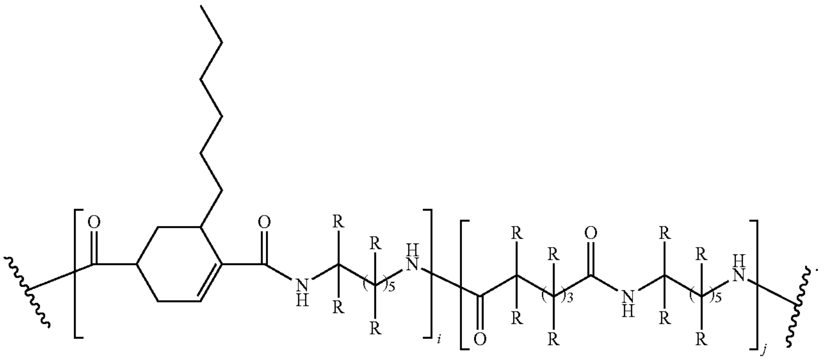

In another embodiment, the polymer of Formula (V) has the structure of Formula (Vk):

(Vk)

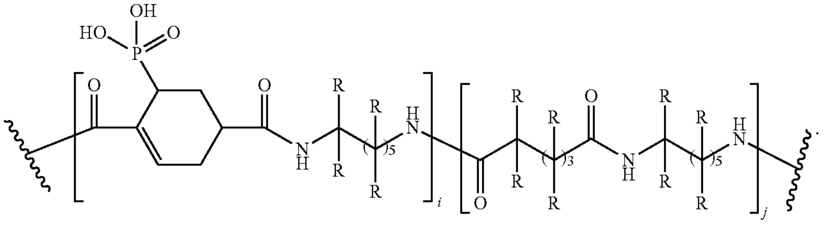

In yet another embodiment, the polymer of Formula (V) has the structure of Formula (VI):

(VI)

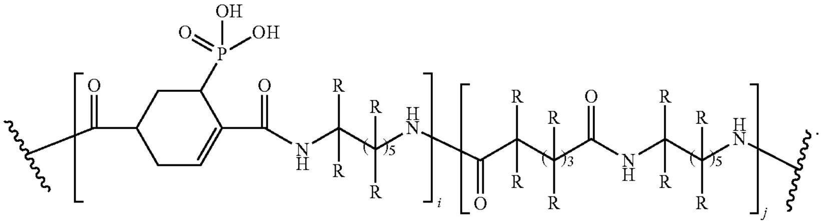

Another aspect of the present application relates to a polymer comprising a moiety:

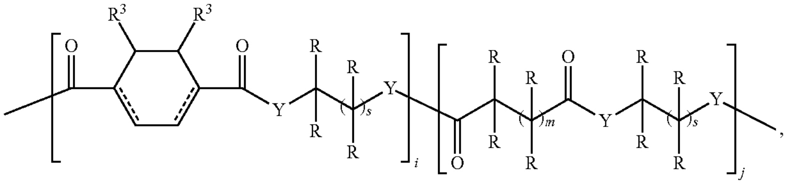

wherein

Y is NH or O;

R is independently selected from the group consisting of H and $C_{1-20}$ alkyl;

each $R^3$ is independently selected from the group consisting of H, $C_{1-20}$ alkyl, aryl, carborane, heteroaryl, heterocyclyl, $C_{1-20}$ alkyl-O—Zn—O—$C_{1-20}$ alkyl, $C_{1-20}$ alkyl-O—Zn—O-heteroaryl, heteroaryl-O—Zn—O-heteroaryl, $C_{1-20}$ alkyl-O—Zn—O-heterocyclyl, heterocyclyl-O—Zn—O-heterocyclyl, heterocyclyl-O—Zn—O-heteroaryl, —$P(O)(R^6)_2$, —$P(O)(OR^5)_2$, —$C_{1-6}$ alkylene-$P(O)(R^6)_2$, and —$C_{1-6}$ alkylene-$P(O)(OR^5)_2$, wherein $C_{1-20}$ alkyl, heteroaryl, and heterocyclyl can be optionally substituted 1 to 3 times with $R^4$;

$R^4$ is selected from the group consisting of H, $C_{1-6}$ alkyl, SH, $NH_2$, $PH_2$, $P(O)(OR^5)_2$, $P(O)(OR^5)_3$, $P(O)(OR^5)_2R^6$, $P(O)(OR^5)(R^6)_2$, $P(O)(R^6)_2$, $BH_2$,

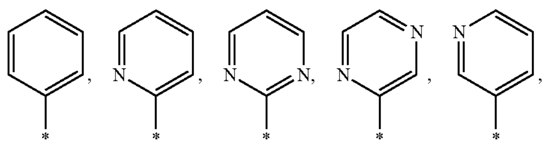

-continued

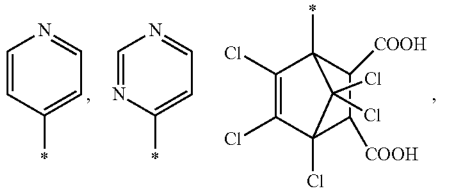

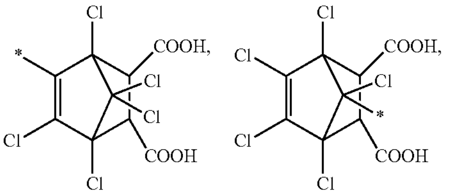

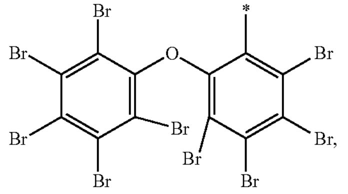

-continued

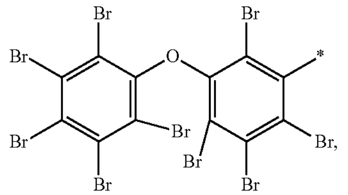

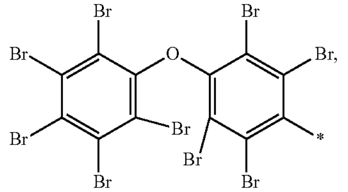

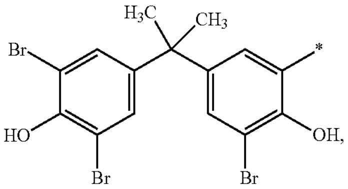

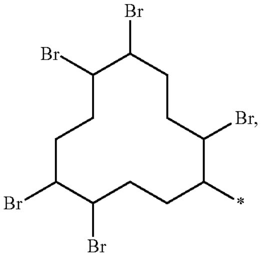

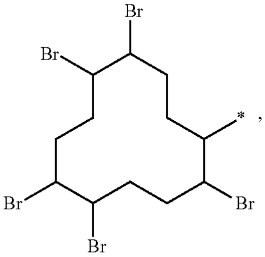 ,

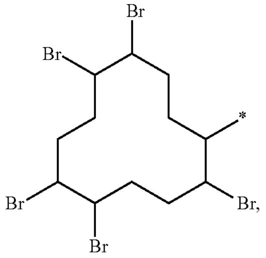

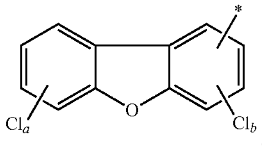 ,

-continued

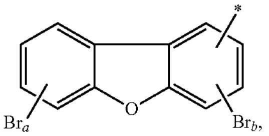

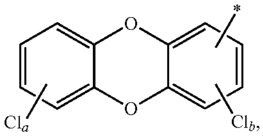

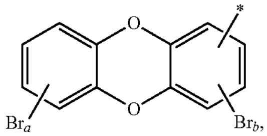

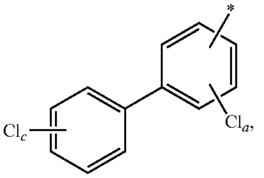 and 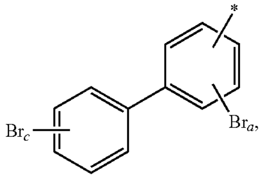

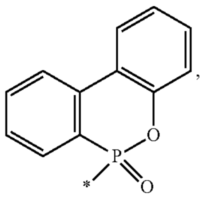 , and 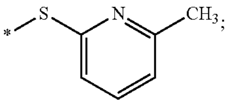

a is 1, 2, 3, or 4;
b is 1, 2, or 3;
c is 1, 2, 3, 4, or 5;
each $R^5$ is independently selected from the group consisting of H, $C_{1-6}$ alkyl, $C_{1-6}$ alkenyl, and aryl, wherein aryl can be optionally substituted 1 to 3 times with halogen, or $C_{1-6}$ alkyl;
each $R^6$ is independently selected from the group consisting of H, $C_{1-6}$ alkyl, $C_{1-6}$ alkenyl, and aryl, wherein aryl can be optionally substituted 1 to 3 times with halogen, or $C_{1-6}$ alkyl,
$\diagup^{*}$ is the point of attachment of $R^4$ to $R^3$;
i is 1 to 1,000,000;
j is 1 to 1,000,000;
m is 0 to 32;
s is 0 to 32; and
$\overline{\underline{---}}$ is a single or a double bond, with only one of $\overline{\underline{---}}$ being a double bond.

Another aspect of the present application relates to a polymer of Formula (V):

(V)

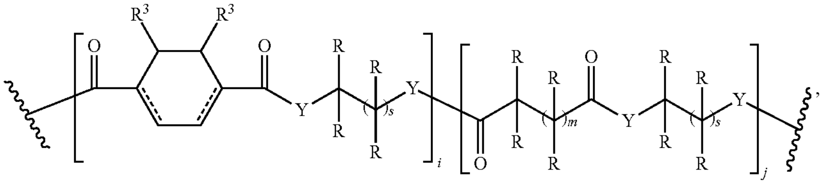

wherein

Y is NH or O;

R is independently selected from the group consisting of H and $C_{1-20}$ alkyl;

each $R^3$ is independently selected from the group consisting of H, $C_{1-20}$ alkyl, aryl, carborane, heteroaryl, heterocyclyl, $C_{1-20}$ alkyl-O—Zn—O—$C_{1-20}$ alkyl, $C_{1-20}$ alkyl-O—Zn—O-heteroaryl, heteroaryl-O—Zn—O-heteroaryl, $C_{1-20}$ alkyl-O—Zn—O-heterocyclyl, heterocyclyl-O—Zn—O-heterocyclyl, heterocyclyl-O—Zn—O-heteroaryl, —P(O)($R^6$)$_2$, —P(O)($OR^5$)$_2$, —$C_{1-6}$ alkylene-P(O)($R^6$)$_2$, and —$C_{1-6}$ alkylene-P(O)($OR^5$)$_2$, wherein $C_{1-20}$ alkyl, heteroaryl, and heterocyclyl can be optionally substituted 1 to 3 times with $R^4$;

$R^4$ is selected from the group consisting of H, $C_{1-6}$ alkyl, SH, $NH_2$, $PH_2$, P(O)($OR^5$)$_2$, P(O)($OR^5$)$_3$, P(O)($OR^5$)$_2R^6$, P(O)($OR^5$)($R^6$)$_2$, P(O)($R^6$)$_2$, $BH_2$,

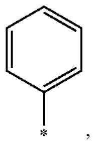,
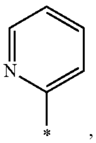,
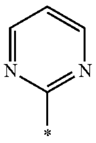,
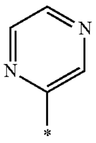,
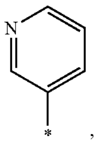,
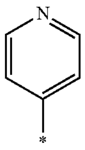,
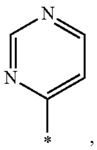,
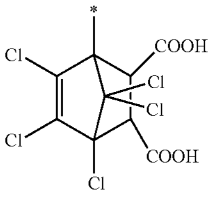,
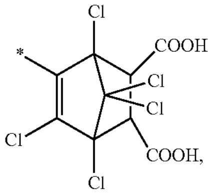
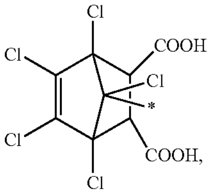
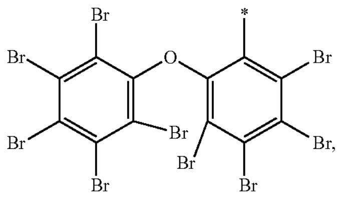
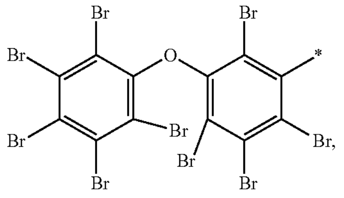
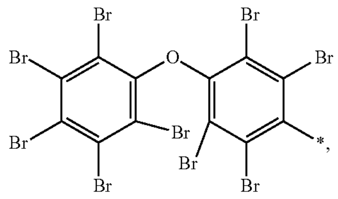

-continued

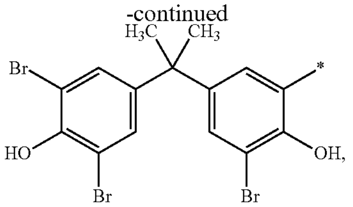
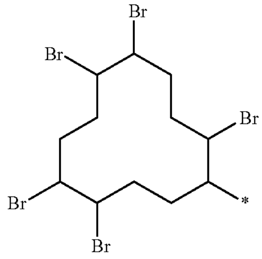,
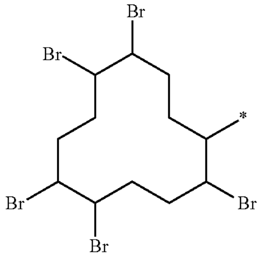,
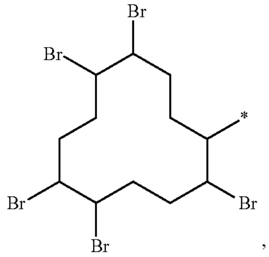,
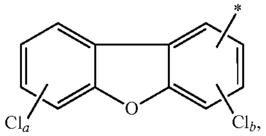
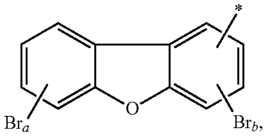
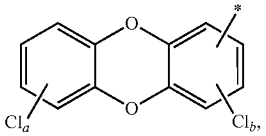
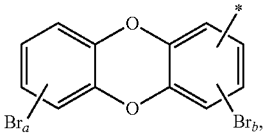
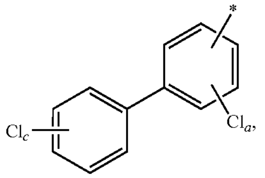 and 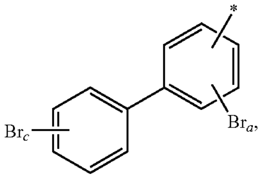
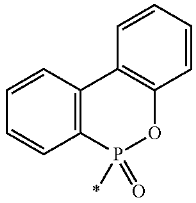, and 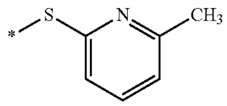;

a is 1, 2, 3, or 4;

b is 1, 2, or 3;

c is 1, 2, 3, 4, or 5;

each $R^5$ is independently selected from the group consisting of H, $C_{1-6}$ alkyl, $C_{1-6}$ alkenyl, and aryl, wherein aryl can be optionally substituted 1 to 3 times with halogen, or $C_{1-6}$ alkyl;

each $R^6$ is independently selected from the group consisting of H, $C_{1-6}$ alkyl, $C_{1-6}$ alkenyl, and aryl, wherein aryl can be optionally substituted 1 to 3 times with halogen, or $C_{1-6}$ alkyl, is the point of attachment of $R^4$ to $R^3$;

i is 1 to 1,000,000;

j is 1 to 1,000,000;
m is 0 to 32;
s is 0 to 32; and

is a terminal group of the polymer;
--- s a single or a double bond, with only one of --- being a double bond.

In one embodiment, the polymer is a statistical polymer.

In another embodiment, the polymer is a random polymer.

In another embodiment, the polymer is an alternating polymer.

In yet another embodiment, the polymer is a block polymer.

According to the present application, i is from 1 to 1,000,000. For example, i is from 2 to 1,000,000, i is from 10 to 1,000,000, i is from 25 to 1,000,000, i is from 50 to 1,000,000, i is from 75 to 1,000,000, i is from 100 to 1,000,000, i is from 150 to 1,000,000, i is from 200 to 1,000,000, i is from 250 to 1,000,000, i is from 300 to 1,000,000, i is from 350 to 1,000,000, i is from 400 to 1,000,000, i is from 450 to 1,000,000, i is from 500 to 1,000,000, i is from 550 to 1,000,000, i is from 600 to 1,000,000, i is from 650 to 1,000,000, i is from 700 to 1,000,000, i is from 750 to 1,000,000, i is from 800 to 1,000,000, i is from 850 to 1,000,000, i is from 900 to 1,000,000, i is from 950 to 1,000,000, i is from 1,000 to 1,000,000, i is from 1,500 to 1,000,000, i is from 2,000 to 1,000,000, i is from 3,000 to 1,000,000, i is from 4,000 to 1,000,000, i is from 5,000 to 1,000,000, i is from 6,000 to 1,000,000, i is from 7,000 to 1,000,000, i is from 8,000 to 1,000,000, i is from 9,000 to 1,000,000, i is from 10,000 to 1,000,000, i is from 20,000 to 1,000,000, i is from 30,000 to 1,000,000, i is from 40,000 to 1,000,000, i is from 50,000 to 1,000,000, i is from 100,000 to 1,000,000, i is from 250,000 to 1,000,000, i is from 500,000 to 1,000,000, i is from 750,000 to 1,000,000. For example, i is from 2 to 850,000, i is from 10 to 700,000, i is from 50 to 600,000, i is from 100 to 500,000, i is from 250 to 500,000, i is from 500 to 500,000, i is from 1,000 to 500,000, i is from 2,000 to 500,000, i is from 10,000 to 500,000, i is from 100,000 to 500,000.

According to the present application, j is from 1 to 1,000,000. For example, j is from 2 to 1,000,000, j is from 10 to 1,000,000, j is from 25 to 1,000,000, j is from 50 to 1,000,000, j is from to 1,000,000, j is from 100 to 1,000,000, j is from 150 to 1,000,000, j is from 200 to 1,000,000, j is from 250 to 1,000,000, j is from 300 to 1,000,000, j is from 350 to 1,000,000, j is from 400 to 1,000,000, j is from 450 to 1,000,000, j is from 500 to 1,000,000, j is from 550 to 1,000,000, j is from 600 to 1,000,000, j is from 650 to 1,000,000, j is from 700 to 1,000,000, j is from 750 to 1,000,000, j is from 800 to 1,000,000, j is from 850 to 1,000,000, j is from 900 to 1,000,000, j is from 950 to 1,000,000, j is from 1,000 to 1,000,000, j is from 1,500 to 1,000,000, j is from 2,000 to 1,000,000, j is from 3,000 to 1,000,000, j is from 4,000 to 1,000,000, j is from 5,000 to 1,000,000, j is from 6,000 to 1,000,000, j is from 7,000 to 1,000,000, j is from 8,000 to 1,000,000, j is from 9,000 to 1,000,000, j is from 10,000 to 1,000,000, j is from 20,000 to 1,000,000, j is from 30,000 to 1,000,000, j is from 40,000 to 1,000,000, j is from 50,000 to 1,000,000, j is from 100,000 to 1,000,000, j is from 250,000 to 1,000,000, j is from 500,000 to 1,000,000, j is from 750,000 to 1,000,000. For example, j is from 2 to 850,000, j is from 10 to 700,000, j is from 50 to 600,000, j is from 100 to 500,000, j is from 250 to 500,000, j is from 500 to 500,000, j is from 1,000 to 500,000, j is from 2,000 to 500,000, j is from 10,000 to 500,000, j is from 100,000 to 500,000.

According to the present application, the polymer can have a number average molecular weight ($M_n$) above 1 kDa, above 2 kDa, above 3 kDa, above 4 kDa, above 5 kDa, above 6 kDa, above 7 kDa, above 8 kDa, above 9 kDa, above 10 kDa, above 11 kDa, above 12 kDa, above 13 kDa, above 14 kDa, above 15 kDa, above 16 kDa, above 17 kDa, above 18 kDa, above 19 kDa, above 20 kDa, above 21 kDa, above 22 kDa, above 23 kDa, above 24 kDa, above 25 kDa, above 26 kDa, above 27 kDa, above 28 kDa, above 29 kDa, above 30 kDa, above 31 kDa, above 32 kDa, above 33 kDa, above 34 kDa, above 35 kDa, above 36 kDa, above 37 kDa, above 38 kDa, above 39 kDa, above 40 kDa, above 41 kDa, above 42 kDa, above 43 kDa, above 44 kDa, above 45 kDa, above 46 kDa, above 47 kDa, above 48 kDa, above 49 kDa, or above 50 kDa.

According to the present application, the polymer can have a number average molecular weight ($M_n$) ranging from 1 kDa to 200 kDa. For example, the polymer can have a number average molecular weight ($M_n$) from 1 kDa to 100 kDa, from 1 kDa to 60 kDa, from 1 kDa to 50 kDa, from 1 kDa to 45 kDa, from 1 kDa to 40 kDa, from 1 kDa to 35 kDa, from 2 kDa to 40 kDa, from 3 kDa to 40 kDa, from 4 kDa to 40 kDa, from 5 kDa to 40 kDa, from 6 kDa to 40 kDa, from 7 kDa to 40 kDa, from 8 kDa to 40 kDa, from 9 kDa to 40 kDa, from 10 kDa to 40 kDa, from 2 kDa to 30 kDa, from 3 kDa to 30 kDa, from 4 kDa to 30 kDa, from 5 kDa to 30 kDa, from 6 kDa to 30 kDa, from 7 kDa to 30 kDa, from 8 kDa to 30 kDa, from 9 kDa to 30 kDa, from 10 kDa to 30 kDa, from 11 kDa to 30 kDa, from 12 kDa to 30 kDa, from 13 kDa to 30 kDa, from 14 kDa to 30 kDa, from 15 kDa to 30 kDa, from 2 kDa to 20 kDa, from 3 kDa to 20 kDa, from 4 kDa to 20 kDa, from 5 kDa to 20 kDa, from 6 kDa to 20 kDa, from 7 kDa to 20 kDa, from 8 kDa to 20 kDa, from 9 kDa to 20 kDa, from 10 kDa to 20 kDa, from 11 kDa to 20 kDa, from 12 kDa to 20 kDa, from 13 kDa to 20 kDa, from 14 kDa to 20 kDa, or from 15 kDa to 20 kDa.

The polymers of Formula (V) exhibit a low degree of water uptake at 50-100% relative humidity. The polymers of Formula (V) may exhibit a degree of water uptake of about 5 wt. % or less, about 2 wt. % or less, about 1 wt. % or less, or about 0.01 wt. % to about 0.5 wt. %.

The above disclosure is general. A more specific description is provided below in the following examples. The examples are described solely for the purpose of illustration and are not intended to limit the scope of the present application. Changes in form and substitution of equivalents are contemplated as circumstances suggest or render expedient. Although specific terms have been employed herein, such terms are intended in a descriptive sense and not for purposes of limitation.

EXAMPLES

The following Examples are presented to illustrate various aspects of the present application, but are not intended to limit the scope of the claimed application.

Example 1—Isomerization of Cyclohexenedicarboxylic Acid and its Derivatives

Cyclo-2-hexene dicarboxylic acid (CH2DA) readily isomerized to cyclo-1-hexene dicarboxylic acid (CH1DA) during Diels-Alder cycloaddition reaction between trans, trans-muconic acid (ttMA) and ethylene using gamma-valerolactone as a solvent. 1 g of ttMA was placed in a Parr micro reactor filled with 35 ml of gamma-valerolactone. The reactor was then charged with 500 psig of ethylene and the reaction was performed at 180° C. for 24 hours. $^1$H NMR in dimethyl sulfoxide (DMSO-d6) indicated >99% yield of CH1DA.

Dimethyl-trans,trans-muconate (1 g) was reacted with 35 ml of 1-octene at 180° C. for 24 hours in a micro reactor pressurized with 150 psig of nitrogen. The corresponding cycloadduct with an unsaturation in the beta-gamma position was then de-esterified using 1M NaOH for 48 hours at 75° C. After reaction, a shift of the unsaturation to the alpha-beta position was observed. Comparison of the integration ratios from $^1$H NMR showed >99% yield to alpha-beta unsaturated diacid.

Example 2—Results of Example 1

The conjugated double bond in Diels-Alder active ttMA can be reacted with ethylene to produce its corresponding cycloadduct, CH2DA (U.S. Pat. No. 8,809,583 to Bui et al.; International Application Publication No. WO 2011/085311 to Bui et al.; U.S. Pat. No. 8,367,859 to Frost et al.; U.S. Application Publication No. 2010/0314243 to Frost et al.; U.S. Pat. No. 8,426,639 to Frost et al.; International Application Publication No. WO 2010/148049 to Frost et al., which are hereby incorporated by reference in their entirety). However, $^1$H NMR analysis of the spectrum in DMSO-d6 showed a shift in the unsaturation to CH1DA as shown in FIG. 1. The position of this alpha-beta unsaturation was confirmed through peak integration ratios, indicating a >99% yield to CH1DA. The shift in the unsaturation was likely due to the stabilization due to conjugation offered by the carboxylic end group.

Figure 2:
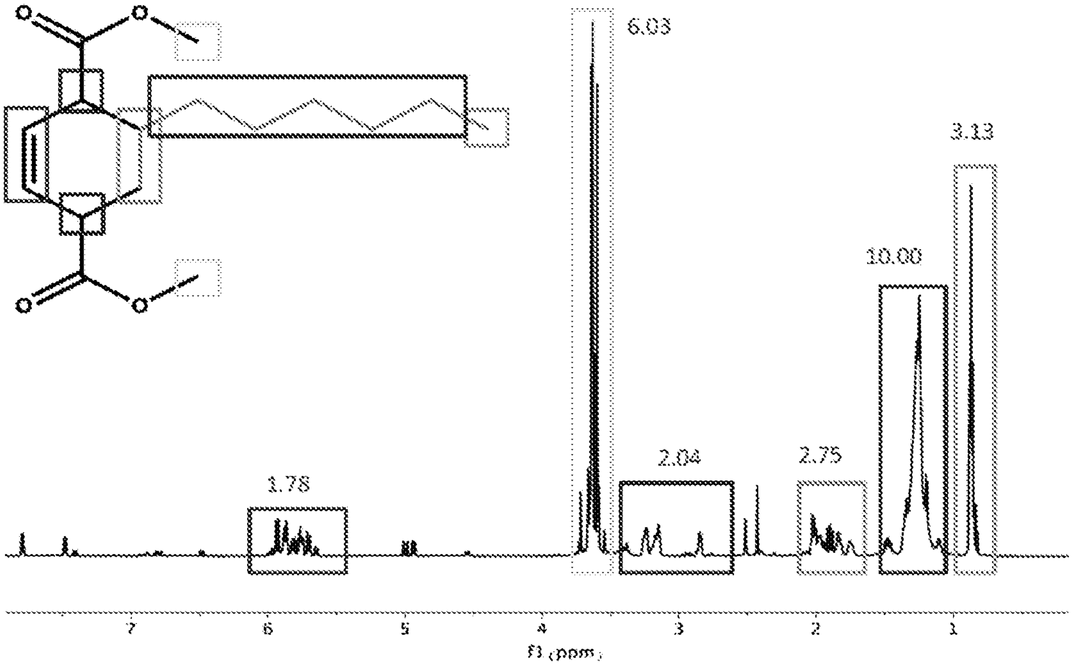
FIG. 2 depicts the $^1H$ NMR spectrum before the shift of unsaturation from beta-gamma to alpha-beta position in the presence of a base.
Figure 3:
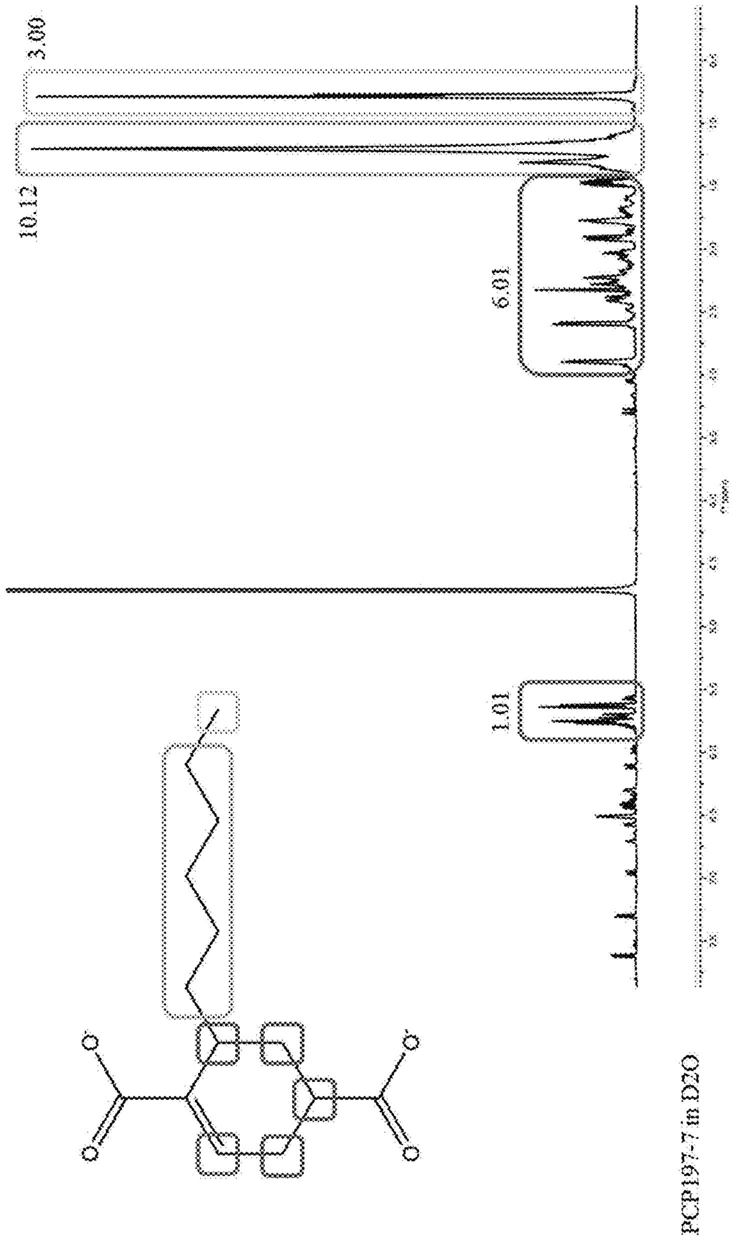
FIG. 3 depicts the $^1H$ NMR spectrum after the shift of unsaturation from beta-gamma to alpha-beta position in the presence of a base.

A similar cycloaddition reaction between ttMA derivative, dimethyl-trans,trans-muconate, occurred with 1-octene (dienophile) to yield a cyclic diester with an unsaturation in beta-gamma position (Scheme 5). Upon a base-catalyzed de-esterification of 0.3 g of the cycloadduct at 75° C., a shift in the double bond was observed as indicated in Scheme 5. The yield to the alpha-beta unsaturated diacid reached >99% after 48 hours in the presence of 4 ml of 1M sodium hydroxide as indicated by $^1$H NMR spectrum in FIGS. 2 and 3. This isomerization in cyclic MA-derivatives was particularly interesting as it not only expands available functionalization chemistries, but also prevents a ring-opening retro Diels-Alder reaction.

Scheme 5. Diels-Alder Cycloaddition Between MA Derivative with Dienophile 1-Octene

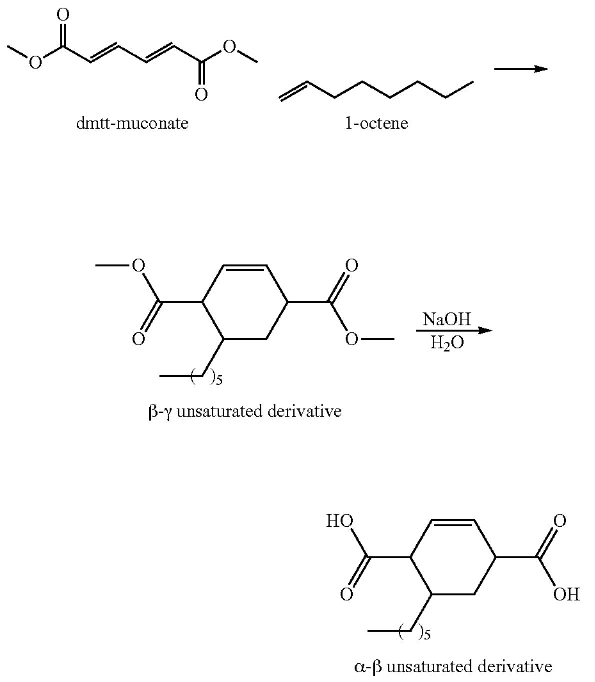

dmtt-muconate 1-octene

β-γ unsaturated derivative

α-β unsaturated derivative

Example 3—Materials for Examples 4-6

Trans,trans-muconic acid (ttMA), gamma-valerolactone, methanol, hexamethylene diamine (HMDA), adipic acid (AA), 1-octene (OC), 1-tetradecene (TD), and potassium hydroxide were purchased from Sigma-Aldrich. Ethyl acetate, hexanes, tetrahydrofuran (THF), and hydrochloric acid were purchased from Fisher Scientific. Chloroform ($CDCl_3$) and dimethyl sulfoxide-d6 (DMSO-$d_6$) were purchased from Cambridge isotopes.

Example 4—Procedure for Monomer Synthesis

The synthesis procedure for the diacids used in the present application is shown in Scheme 6. Cyclo-hex-1-ene-1,4-dicarboxylic acid (CH1DA) was synthesized using 1 g of ttMA in 35 ml of gamma-valerolactone. The reactor was then charged with 500 psig of ethylene and the reaction was performed at 180° C. for 24 hours. $^1$H NMR in dimethyl sulfoxide (DMSO-d6) indicated complete conversion of ttMA to CH1DA. Dimethyl-trans,trans-muconate (dmttm) was prepared using 0.1 M ttMA in methanol through an acid catalyzed method. p-Toluenesulfonic acid (1 wt %) was added to the solution in a three-neck round bottom flask with an attached reflux column and was heated to 63° C. for 48 hours. Subsequently, the product was filtered and washed with DMSO to remove any unreacted ttMA (71.9% yield). The product was dried in a vacuum oven and dissolved in $CDCl_3$ and analyzed through $^1$HNMR.

Scheme 6. Synthesis of Novel Hydrophobic Diacids Using Diels-Alder Chemistry from ttMA

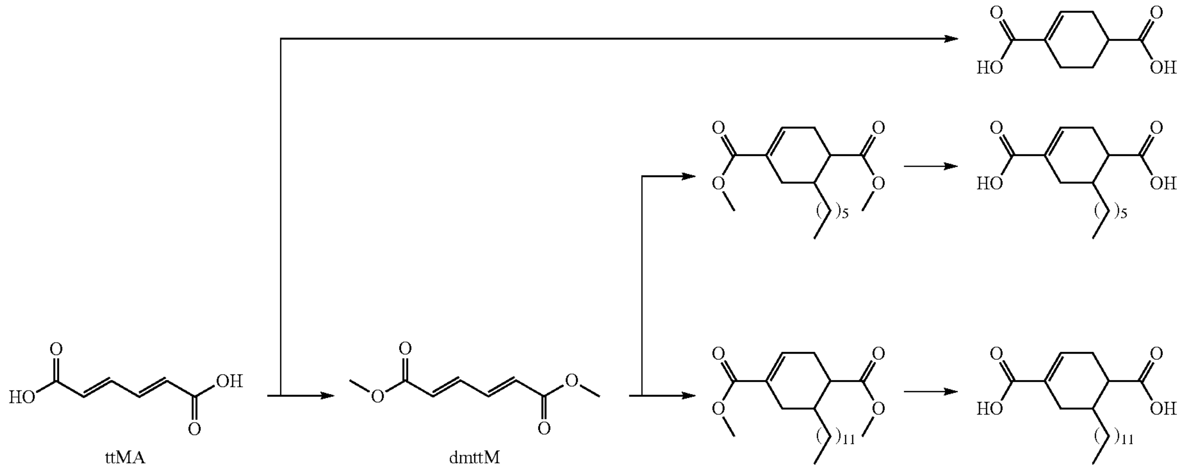

ttMA dmttM

Figure 4:
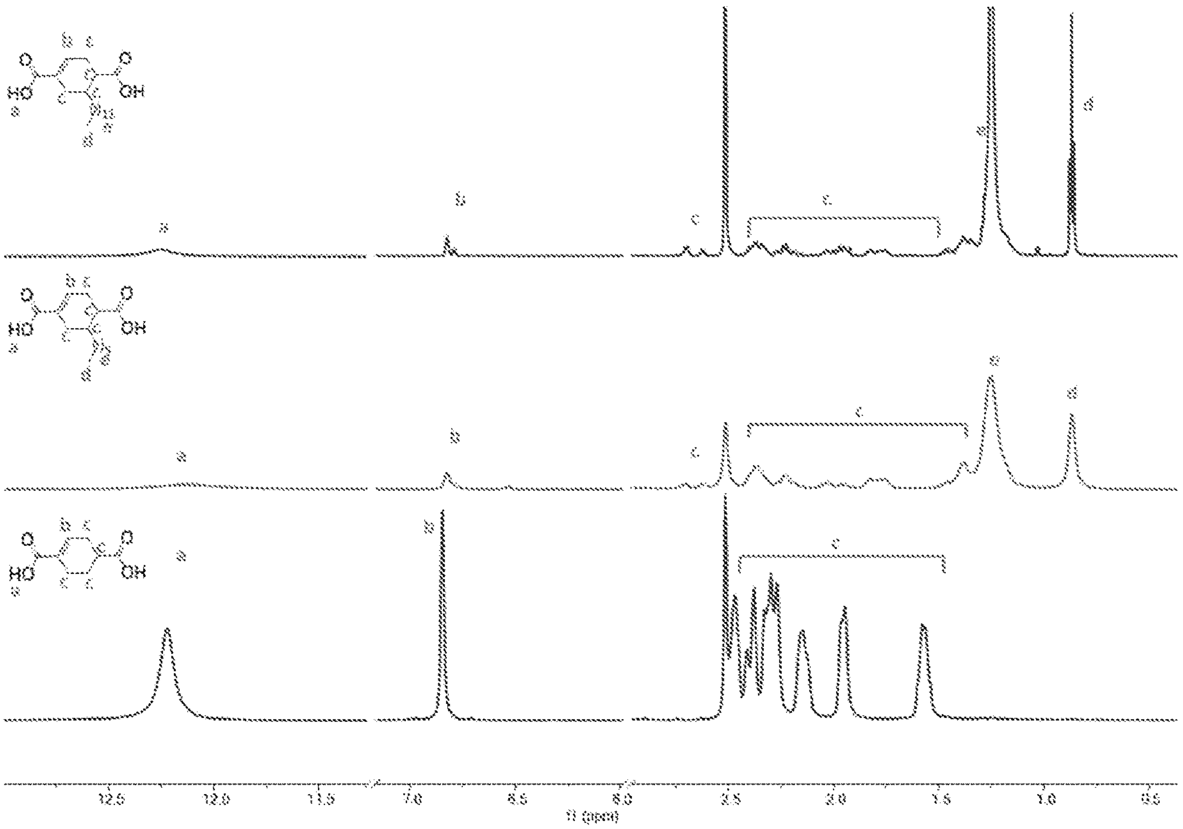
FIG. 4 depicts the $^1H$ NMR spectra for alkyl-chain functionalized dicarboxylic acids in DMSO-$d_6$ at 600 MHz.

Diels-Alder reactions between the 3 g of diester and the 35 ml of vinyl-bearing compounds (1-octene and 1-tetradecene) were carried out under 150 psig $N_2$ environment at 180° C. for 24 hours. GC/MS showed complete conversion of dmttm and the formation of the cyclo-adducts with 74.7% yield for 1-octene and 67% yield for 1-tetradecene. The product was extracted from the vinyl-bearing reactant using a Biotage flash chromatography system using hexane and ethyl acetate as solvents. Upon isolating the desired fraction, the remaining hexane and ethyl acetate were evaporated using a Buchi R-205 rotovap. Next, these cyclic diesters were hydrolyzed using 200 ml of 1 M sodium hydroxide at 75° C. for 72 hours. Products were isolated by reducing the pH of the reaction mixture through hydrochloric acid workup and washing the product precipitate with water to remove any remaining acid (yields: 88.7% for 1-octene and 63% for 1-tetradecene). The final diacids were dried overnight in a vacuum oven. $^{1}H$ NMR was carried out on the dried product in DMSO-$d_6$ (FIG. 4 and Table 1).

TABLE 1

Comparison Between Expected and Observed Peak Integrations

| Sample | Peaks[a] | Expected | Observed |
|---|---|---|---|
| CH1DA | a | 2 | 1.9 |
| | b | 1 | 1 |
| | c | 7 | 7.1 |
| CH1DA-OC | a | 2 | 1.6 |
| | b | 1 | 1 |
| | c | 6 | 5.9 |
| | d | 3 | 3 |
| | e | 10 | 10.1 |
| CH1DA-TD | a | 2 | 1.7 |
| | b | 1 | 0.7 |
| | c | 6 | 6 |
| | d | 3 | 3 |
| | e | 22 | 21.5 |

TABLE 1-continued

[a]Peaks assigned based on FIG. 4

Example 5—Salt and Polyamide Synthesis

Salt formation between HMDA and the dicarboxylic acids (CH1DA/CH1DA-OC/CH1DA-TD) were carried out to ensure stoichiometric equivalence. Conventional nylon-6,6 salt was prepared between AA and HMDA by dissolving them in methanol. The two solutions were mixed and allowed to react for 1 hour at 40° C. The precipitated salt was filtered, washed repeatedly with methanol, and dried overnight in the fume hood. Salts between the synthesized dicarboxylic acids and HMDA were prepared similarly but using THE as solvent, due to the low solubility of these novel molecules in methanol.

After isolating the dried salts, they were combined at 25 mol % novel diacid salt and 75 mol % conventional nylon-6,6 salt. 60 wt % DI water was added to this salt mixture to assist in the formation of oligomers. Temperature control for polymerization was maintained through an external thermocouple and the mixture was stirred at 400 rpm. To maintain inert conditions, the vessel was initially purged five times and then charged to 150 psig of nitrogen. The temperature of the vessel was then held at an external temperature of 265° C. for 2 hours followed by a vent out. Venting out resulted in removal of water formed as a byproduct of polycondensation, shifting the equilibrium towards longer chain polymers. Finally, the temperature was increased to 300° C. and held there for 1 hour. On completion of polymerization, the vessel was allowed to return to room temperature before extracting the polyamide.

Scheme 7. Synthesis of Hydrophobic Polyamides

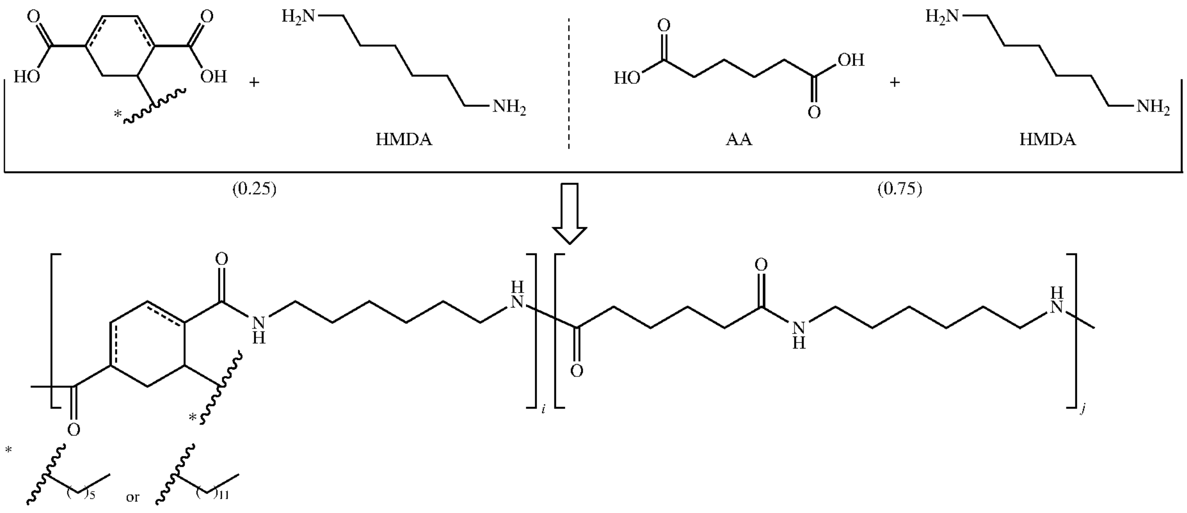

In Scheme 7, individual salts were prepared between hydrophobic diacid:HMDA in THF and AA:HMDA in methanol. Subsequently, 25 mol % of novel salt was mixed with 75 mol % of nylon-6,6 salt and polymerized.

Example 6—Polymer Characterization

Monomer Incorporation

Monomer incorporation into the polyamide backbone was characterized using elemental analysis and $^1H$ NMR. Elemental analysis was carried out on around 2-4 mg of polymer sample using Thermo Flash Smart 2000 CHNS/O Elemental Analyzer. $^1H$ NMR was carried out on the Bruker AVIII600. Polymer samples of around 15 mg were cut and dissolved in a 2:3 (v:v) mixture of trifluoroacetic anhydride and $CDCl_3$. Percent incorporation was calculated by subtracting the nylon-6,6 peaks, integrating the residual peaks, and normalizing them to the overall integral.

Gel Permeation Chromatography

Molecular weights of the polyamide series were determined using an EcoSEC gel permeation chromatography (GPC) system equipped with refractive index and UV detectors. Polymer samples of 5 mg were dissolved overnight in 1,1,1,3,3,3-hexafluoroisopropanol (HFIP). Prior to injection, the samples were passed through a 0.45 μm PTFE filter. The columns for the GPC included a Tosoh TSKgel SuperH6000 in series with two Agilent PL HFIP gel columns. Sample aggregation was prevented by using HFIP in combination with sodium trifluoroacetate at a concentration of 0.02 mol/L HFIP (1.7 g/kg HFIP). Sample injection volume of 10 μL was analyzed at 45° C. under a 0.3 m/min flow rate.

Thermal Properties

Analysis of thermal properties was carried out using differential scanning calorimetry (DSC) and thermogravimetric analysis (TGA). DSC was conducted in a TA DSC2500 instrument with 3-5 mg samples placed in crimped aluminum hermetic pans. Samples were held isothermally for 2 minutes at 150° C. and cycled thrice between 150° C. and 300° C. at 10 K/min under nitrogen gas to remove the thermal history of the polymers. Data was analyzed using the Trios software.

TGA was performed using a Netzsch STA449 F1 instrument and data analysis was done using the Proteus software. 5-10 mg of polyamide samples were placed in alumina pans. The temperature program included an isothermal stage of 80° C. for 5 minutes, followed by a 10K/min ramp to 700° C. under nitrogen. Residual char was measured at 500° C.

Crystal Structure Determination

The polyamide series were injection molded using a Haake MiniLab extruder into ISO 527-2-1BB model samples. The specimens were annealed in a vacuum oven for 6 hours at 150° C. and were allowed to cool down to room temperature overnight. Wide-angle X-ray scattering (WAXS) diffractograms were collected with a XENOCS Xeuss 2.0 SWAXS system with monochromatized light ($\lambda$=1.54 Å) from Cu K$\alpha$ radiation. The percent crystallinities of samples were calculated using MDI Jade 6 software through integrating sharp peaks with respect to the total integral.

Water Absorption Tests

The water uptake and moisture absorption tests were carried out on polymers extruded into ISO 527-2-1BB model samples. Prior to the test, the samples were dried using a vacuum oven at 60° C. for 48 hours. Next, the weight of the dried samples were measured using a Mettler Toledo microbalance with a precision of ±0.1 mg. For the water uptake test, the molded specimens were immersed in an 18.2 MΩ DI water for 24 hours. The samples were gently patted dry and weighed immediately after. Moisture absorption at 50% relative humidity was observed by placing polymer samples in a desiccator with a saturated solution of magnesium nitrate. The desiccator was then placed in an oven for 24 hours at 35° C. For both tests, absorption was calculated using the following equation:

$$A = \frac{(W-D)}{D} * 100\% \quad A = \frac{(W-D)}{D} * 100\% \qquad \text{Eq. 1}$$

where:

A=Water/moisture absorption, %

W=Weight of wet sample, g

D=Weight of dried sample, g

Contact Angle Tests

Contact angle tests were carried out by placing tensile bars of polymer samples and securing them on a level surface. Equal surface roughness was ensured through a profilometer. 6 drops of 5 μL of DI water were placed on each sample and pictures were taken within 30 seconds. The images were then analyzed using ImageJ software to measure the contact angle.

Mechanical Properties

TA Ares G2 was used in torsion mode for dynamic mechanical analysis (DMA) of the annealed polyamide samples. The experiment was performed from 0° C. to 90° C. at a 5 K/min ramp in the linear viscoelastic regime with an angular frequency, ω=10 rad $s^{-1}$. The data was analyzed using Trios software.

Example 7—Results of Examples 4-6

Monomer Incorporation into the Polyamide

Figure 5:
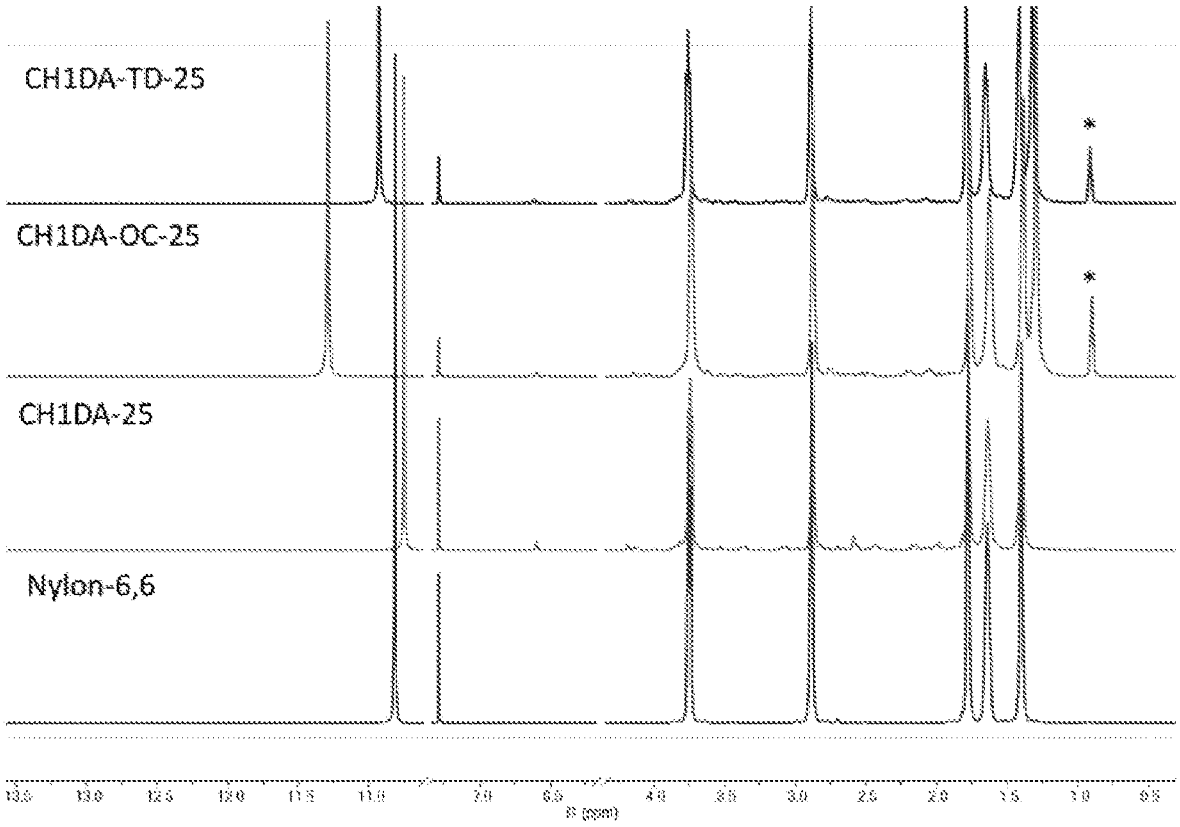
FIG. 5 depicts the $^1H$ NMR spectra in $CDCl_3$ showing successful incorporation of cyclic monomers in polyamide backbone. % Incorporation was calculated by integrating peaks labelled * with respect to hexamethylene diamine (HMDA) peak.

Monomer incorporation was calculated for the synthesized polymers using the $^{1}$H-NMR data by subtracting the nylon-6,6 peaks from the spectrum, integrating the remaining peaks, and normalizing it to the sum of all peaks. Around 20-23 mol % incorporation was observed for the novel diacids into the backbone of the polymer (Table 2). In particular, the survival of the aliphatic pendant groups during the harsh conditions of polymerization was confirmed by the NMR spectra (FIG. 5).

Elemental analysis of these novel polyamides was expected to show an increased carbon atom content (C %) due to the incorporation of the cyclic ring as well as the various pendant groups. The polyamides functionalized with the aliphatic chains (CH1DA-OC-25 and CH1DA-TD-25) closely exhibited the predicted trend. $A_n$ increase in C % and H % was observed along with a decrease in N % due to the long aliphatic chains in these polymers.

TABLE 2

Theoretical and Actual Incorporation of Hydrophobic Polyamides Into Nylon-6,6 Backbone

| | Loading composition (mol %) | | | Elemental Analysis | | | Monomer |
|---|---|---|---|---|---|---|---|
| Sample | AA:HMDA | Cyclic diacid:HMDA | | C % | H % | N % | Incorporation[a] |
| Nylon-6,6 | 100 | 0 | Expected | 63.69 | 9.80 | 12.38 | — |
| | | | Observed | 63.15 | 9.98 | 12.10 | |
| CH1DA-25 | 75 | 25 | Expected | 64.56 | 9.57 | 12.08 | 0.25 |
| | | | Observed | 63.61 | 9.44 | 11.34 | 0.20 |
| CH1DA-OC-25 | 75 | 25 | Expected | 65.72 | 9.91 | 11.38 | 0.25 |
| | | | Observed | 65.52 | 9.77 | 11.06 | 0.23 |
| CH1DA-TD-25 | 75 | 25 | Expected | 66.42 | 10.12 | 10.96 | 0.25 |
| | | | Observed | 68.86 | 10.57 | 10.60 | 0.23 |

[a]Incorporation of cyclic monomer was calculated from $^{1}$H-NMR by integrating an isolated peak with respect to a HMDA diamine peak.

Molecular-Weights of Polymer Series

Figure 6:
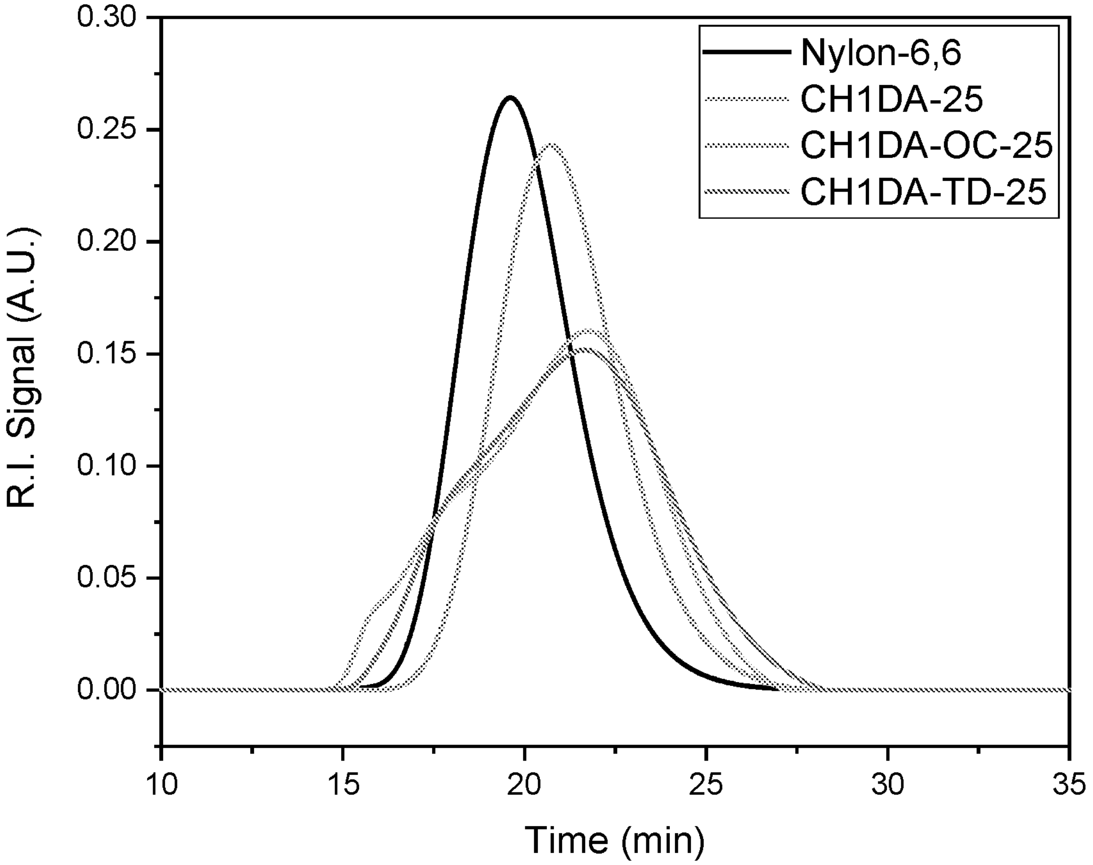
FIG. 6 shows gel permeation chromatography (GPC) trace of polyamides polymerized under similar conditions in a 1,1,1,3,3,3-hexafluoroisopropanol (HFIP) system.

The GPC trace of the polyamide series is shown in FIG. 6. Molecular weights were calculated with respect to PMMA standards and are displayed in Table 3. Under similar polymerization conditions, nylon-6,6 exhibited the highest molecular weight ($M_n$=34.3 kDa) with a dispersity (Đ) of 2. The cyclo-aliphatic polyamides showed a decrease in $M_n$, which could be due to the difference in reaction kinetics between the novel dicarboxylic acids and adipic acid. The alpha-olefin functionalized diacids (CH1DA-OC-25 and CH1DA-TD-25) both showed a fairly high Đ. A possible explanation could be that the asymmetric conjugated unsaturation along with the non-polar pendant groups promoted these dicarboxylic acids to undergo chain transfer more readily than standard nylon-6,6.

TABLE 3

Summary of Molecular Weights, Thermal, and Crystalline Properties of Novel Polyamides

| Sample | Mn[a] (kDa) | Mw[a] (kDa) | Đ[a] | $T_m$ [° C.] | $\Delta H_m$ [J/g] | $T_c$ [° C.] | $\chi_{C\_DSC}$ [%] | $\chi_{C\_WAXS}$ [%] | $Char_{500° C.}$ [%] | $T_{d10}$ [° C.] |
|---|---|---|---|---|---|---|---|---|---|---|
| Nylon-6,6 | 34.3 | 67.8 | 2.0 | 262.2 | 67.2 | 231.4 | 26.3 | 41.5 | 4.1 | 412.5 |
| CH1DA-25 | 21.6 | 41.3 | 1.9 | 245.9 | 46.2 | 209.7 | 18.1 | 39.3 | 3.4 | 412.5 |

TABLE 3-continued

Summary of Molecular Weights, Thermal, and Crystalline Properties of Novel Polyamides

| Sample | Mn[a] (kDa) | Mw[a] (kDa) | Đ[a] | $T_m$ [° C.] | $\Delta H_m$ [J/g] | $T_c$ [° C.] | $\chi_{C\_DSC}$ [%] | $\chi_{C\_WAXS}$ [%] | $Char_{500° C.}$ [%] | $T_{d10}$ [° C.] |
|---|---|---|---|---|---|---|---|---|---|---|
| CH1DA-OC-25 | 12.4 | 61.2 | 4.9 | 228.1 | 29.9 | 177.7 | 11.7 | 37.2 | 2.4 | 410.0 |
| CH1DA-TD-25 | 15.5 | 80.9 | 5.2 | 231.6 | 30.6 | 190.6 | 12.0 | 27.0 | 2.5 | 410.9 |

Figure 7:
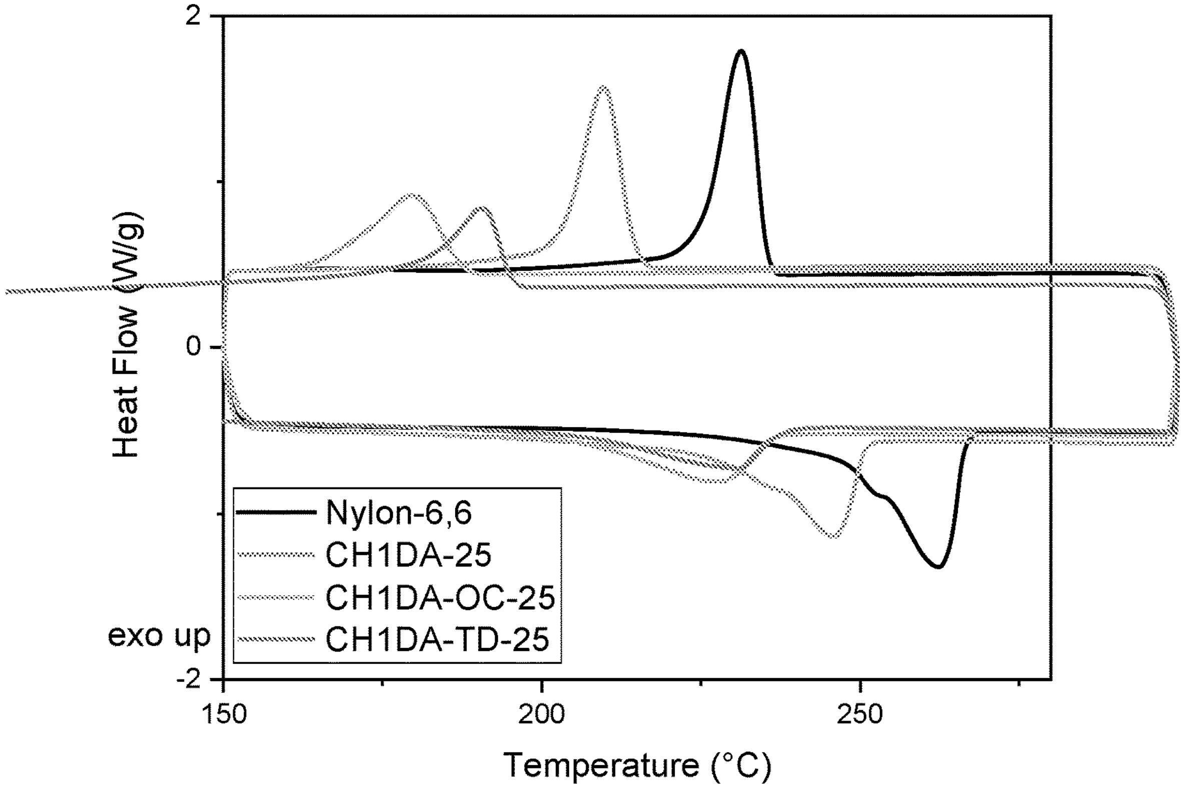
FIG. 7 shows differential scanning calorimetry (DSC) trace for $3^{rd}$ cycle of novel polyamides showing melting point depression on introduction of functionalized cyclic molecules.

[a]Mn: Number-average molecular weight;
Mw: Weight-average molecular weight;
Đ: Dispersity calculated from GPC
[b]$T_m$: Melting temperature;
$T_c$: Crystallization temperature;
$\Delta H_c$: Enthalpy of crystallization;
$\chi_{c\_DSC}$: Percent crystallinity from DSC
[c]$\chi_{c\_WAXS}$: Percent crystallinity from WAXS for annealed samples
[g]$Char_{500° C.}$: Residual mass at 500° C.;
$T_{d10}$: Decomposition temperature at 10% mass loss Crystallinity and Thermal Properties of the Polymer Series The effect of the cycloaliphatic polyamides with pendant groups on thermal properties and crystallinity was investigated using differential scanning calorimetry (DSC), wide-angle X-ray scattering (WAXS), and thermogravimetric analysis (TGA) (Table 3). The overlay of the DSC trace (FIG. 7) shows the 3$^{rd}$ cycle of heating/cooling to remove any effect from the thermal history of the polymer. With its symmetric nature, nylon-6,6 exhibits the highest melting temperature ($T_m$) and degree of crystallinity ($\chi_C$). It was expected that the addition of cyclic diacids would increase chain-length between amide linkages, creating defects and leading to reduced crystallinity. This was evident from the DSC trace of CH1DA-25, which showed a melting point depression of 17° C. and reduced enthalpy of melting ($\Delta H_m$) due to the disruptive nature of the cyclic commoners. The cycloaliphatic polymers with long alkyl chains (CH1DA-OC-25 and CH1DA-TD-25) showed comparable $\chi_{C\_DSC}$ and $T_m$, indicating that the chain-length of pendant groups had minimal effect on the melting point.

Figure 8:
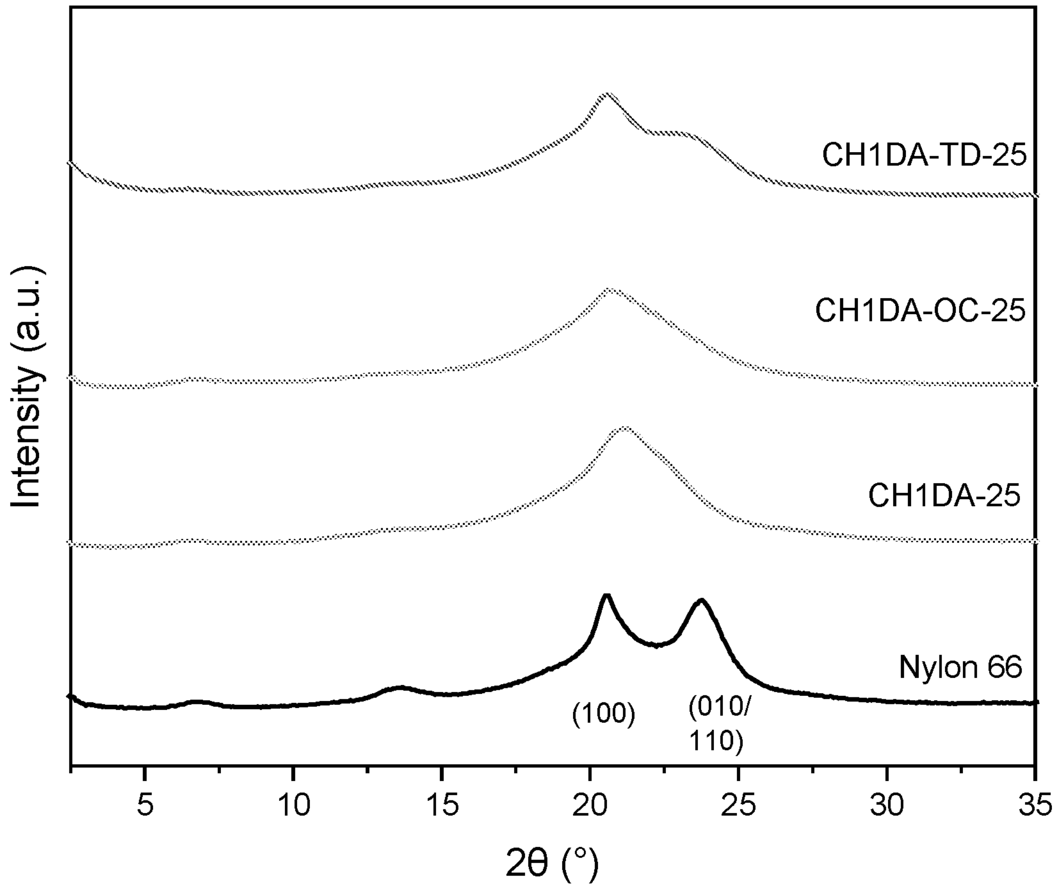
FIG. 8 is a graph showing room temperature (25° C.) wide-angle X-ray scattering (WAXS) pattern for novel polyamides annealed at 160° C. for 6 hours.

To further evaluate the crystalline structure, room temperature WAXS was performed (FIG. 8). The semi-crystalline nature of these polyamides was confirmed by the sharp peaks representing the crystalline segments and the broad halo representing the amorphous regions. The percent crystallinity ($\chi_{C\_WAXS}$) was calculated from the ratio between the areas under the peaks normalized over the total area. It was expected that crystallinity of the copolymers would be lower than that of the nylon homopolymer. Nylon-6,6 exhibited two prominent peaks at approximately at 20° and 24°, corresponding to the (100) and (010)/(110) doublet of the α-phase. Nylon-6,6 possesses a triclinic structure, in which the (100) peak represents intrasheet scattering caused by adjacent polymer chains in a sheet and (010)/(110) peak corresponds to the intersheet scattering between different polymer sheets. As expected, crystallinity of the cycloaliphatic polyamides were lower than neat nylon-6,6 possibly due to exclusion of the functionalized monomers from the crystals. CH1DA-25 and CH1DA-OC-25 showed one broad peak for intrasheet scattering at around 21° whereas CH1DA-TD-25 showed a small shoulder for the scattering of (010)/(110) plane. The results between $\chi_{C\_DSC}$ and $\chi_{C\_WAXS}$ followed similar trend.

Figure 9:
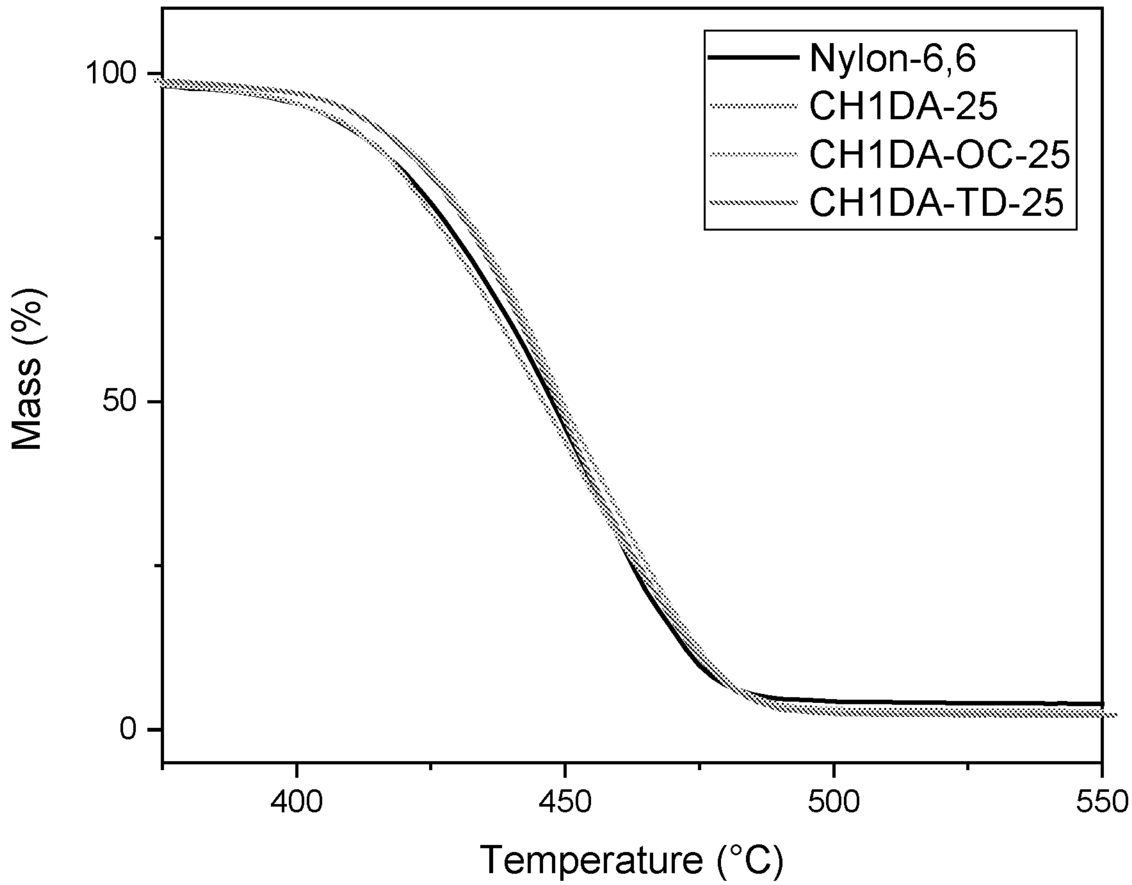
FIG. 9 is a thermogravimetric analysis (TGA) curve showing behavior of polyamides in $N_2$ environment at 10 K/min ramp.

The TGA curve for the polyamide series are shown in FIG. 9. TGA under nitrogen showed that the degradation temperature ($T_{d10}$) was unaffected on inserting a cyclic molecule into the backbone of nylon-6,6 (Table 2). The base case of neat nylon-6,6 demonstrated a char yield of 4.1% at 500° C. It was expected that the hydrocarbon-rich, alkyl-chain functionalized polyamides (CH1DA-OC/TD-25) would show the lowest char, which was confirmed experimentally.

Water Uptake (WU) at 100% and 50% Relative Humidity

Results from the waster absorption tests are shown in Table 4. It is evident that the introduction of non-polar alkyl-chains into the polyamide backbone reduced WU of the polymers compared to nylon-6,6. CH1DA-OC-25 decreased WU by half at 50% RH, but did not show significant improvement at 100% RH. Whereas, CH1DA-TD-25 showed a significant property enhancement, decreasing the WU by over 3-folds at both 50% and 100% RH.

Contact Angle Tests

Contact angle (CA) tests were carried out by placing tensile bars of polymer samples and securing them on a level surface. Equal surface roughness was ensured using a profilometer. 6 drops of 5 μL of DI water were placed on each sample and pictures were taken within 30 seconds. The images were then analyzed using ImageJ software to measure the contact angle. Results are shown in Table 4, where a higher CA corresponds to a more hydrophobic polymer. Both CH1DA-OC-25 and CH1DA-TD-25 performed similarly and showed improvements with respect to nylon-6,6.

TABLE 4

Water Uptake and Contact Angle Test Results of Novel Polyamides and Lab-Synthesized Nylon-6,6

| Samples | Water Uptake Test 50% RH | Water Uptake Test 100% RH | Contact Angle Test Angle [°] |
|---|---|---|---|
| Nylon-6,6 | 1.1 ± 0.7 | 2.5 ± 0.7 | 74.90 ± 2.33 |
| CH1DA-25 | 0.45 ± 0.1 | 2.6 ± 0.5 | 83.27 ± 0.78 |
| CH1DA-OC-25 | 0.57 ± 0.04 | 2.2 ± 0.1 | 86.56 ± 1.40 |
| CH1DA-TD-25 | 0.36 ± 0.05 | 0.8 ± 0.2 | 87.76 ± 2.20 |

Mechanical Properties

Torsional dynamic mechanical analysis (DMA) was conducted to study the viscoelastic response of these polyamides to a known deformation as function of temperature. Values for the storage modulus (E'), loss modulus (E"), and tan δ are summarized in Table 5. E' and E" were reported at the glassy plateau of 0° C. The ratio between E' and E" is given by tan δ, where δ is the phase angle between the stress and the strain. The glass-transition temperature of the polymers ($T_g$) was located using the maxima of tan δ. $T_g$ is characterized as the temperature at which long-range motion in the amorphous domains cease as a polymer melt is cooled. Over this transition, dramatic changes in properties were observed as the polymer shifts from a rubbery to glassy state.

$T_g$ is strongly influenced by the flexibility and molecular mobility of the polymer backbone and their pendant groups. For instance, unfunctionalized cycloaliphatic polyamide (CH1DA-25) had higher E' and $T_g$ than nylon-6,6 due to the reduced flexibility introduced by the cyclic counits. Next, the introduction of alkyl pendant groups of different chain lengths (CH1DA-OC-25 and CH1DA-TD-25) was studied. Two opposing effects were expected to occur with alkyl chains of differing lengths. On one hand, chain mobility is restricted due to steric hindrance causing a rise in $T_g$, whereas an opposing plasticizing behavior dependent on chain-length decreases $T_g$. The latter effect was observed with these two samples, where the 12-C alkyl pendant group had a slightly depressed $T_g$ of 75° C. compared to the 6-C alkyl chain (79° C.). Additionally, both samples exhibited a higher $T_g$ than the base case of nylon-6,6 due to the restricted chain mobility imposed by the functionalized counits. The samples containing aromatic pendant groups (CH1DA-AB-25 and CHDA-AB-25) were expected to exhibit increased $T_g$ as bulky side groups hinder chain rotation.

TABLE 5

Torsional DMA Results of Polyamides Showing Storage and Loss Moduli and Glass Transition Temperature

| Sample | E'[a] [GPa] | E"[a] [MPa] | $T_g$[b] [° C.] |
|---|---|---|---|
| Nylon-6,6 | 1.32 | 16.5 | 73.3 |
| CH1DA-25 | 1.65 | 10.9 | 80.3 |
| CH1DA-OC-25 | 1.55 | 18.6 | 78.6 |
| CH1DA-TD-25 | 1.42 | 15.6 | 74.8 |

[a]E' and E" refers to storage modulus and loss modulus respectively calculated at 0° C.
[b]$T_g$ was calculated at the peak of the tan (δ) curve Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A process of making a polymer of Formula (V):

(V)

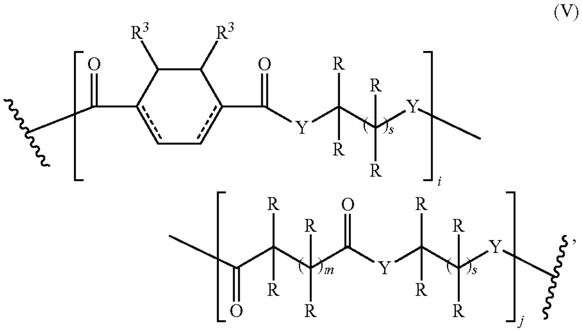

wherein

Y is NH or O;

R is independently selected from the group consisting of H and $C_{1-20}$ alkyl;

each $R^3$ is independently selected from the group consisting of H, $C_{1-20}$ alkyl, and $P(O)(OR^5)_2$;

wherein at least one $R^3$ is not H;

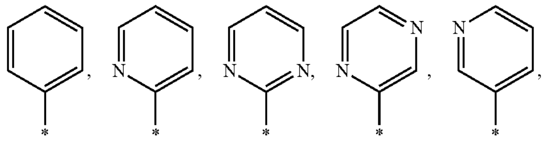

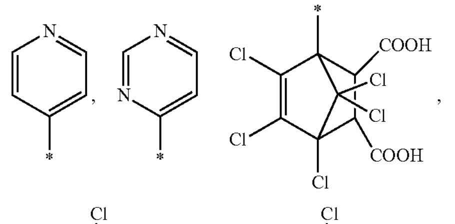

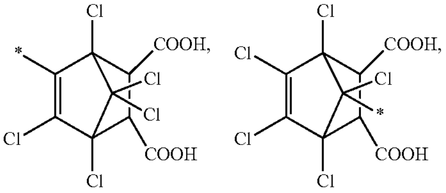

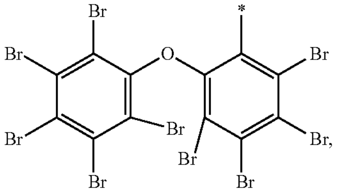

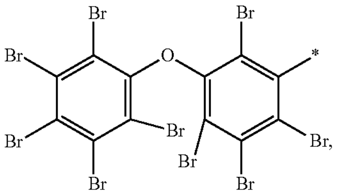

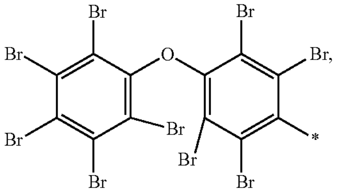

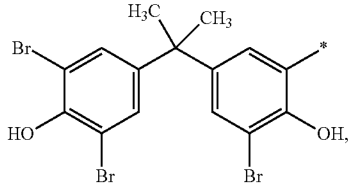

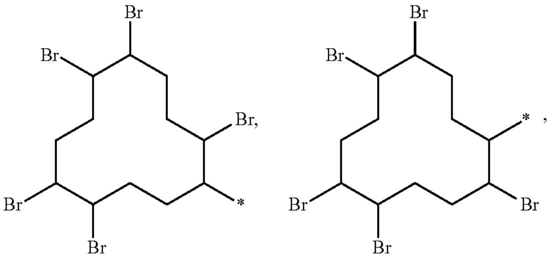

-continued

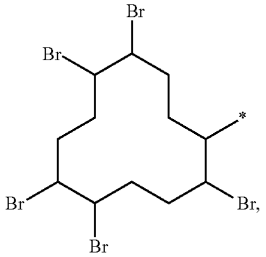

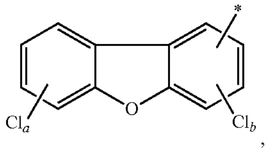

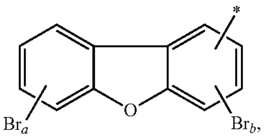

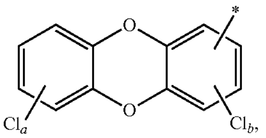

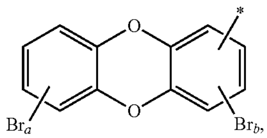

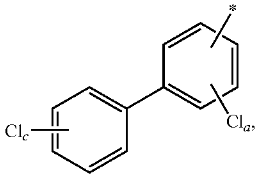

and

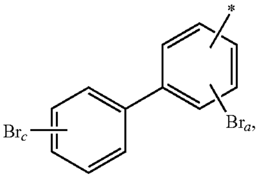

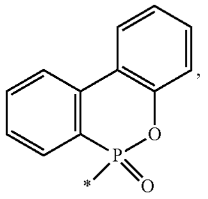

and

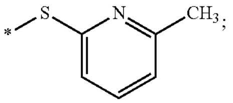

i is 1 to 1,000,000;

j is 1 to 1,000,000;

m is 0 to 32;

s is 0 to 32; and

is a terminal group of the polymer;

═══ is a single or a double bond, with only one ═══ being a double bond, said process comprising:

providing a compound having the structure of Formula (I):

(I)

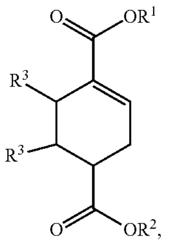

or a salt thereof, wherein $R^1$ is H or $C_{1-6}$ alkyl; and $R^2$ is H or $C_{1-6}$ alkyl; and providing a compound having the structure of Formula (VI):

(VI)

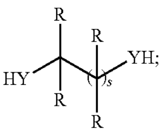

providing a compound having the structure of Formula (VII):

(VII)

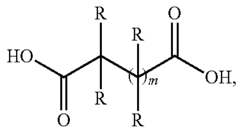

and reacting the compound of Formula (I), the compound of Formula (VI), and the compound of Formula (VII) under conditions effective to produce the polymer of Formula (V).

2. A polymer of Formula (V):

(V)

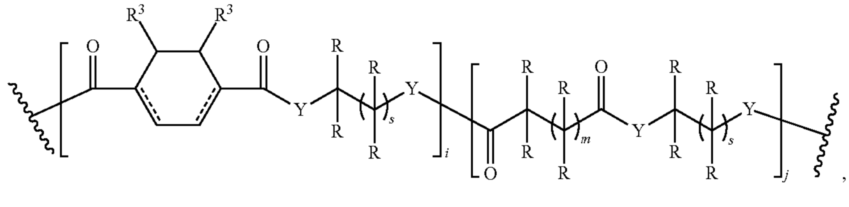

wherein

Y is NH or O;

R is independently selected from the group consisting of H and $C_{1-20}$ alkyl;

each $R^3$ is independently selected from the group consisting of H, $C_{1-20}$ alkyl, and wherein at least one $R^3$ is not H;
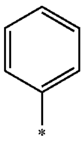,
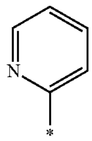,
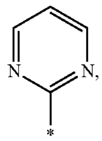
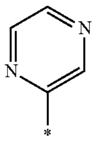,
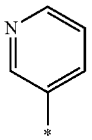,
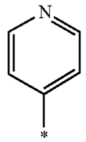,
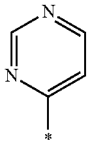,
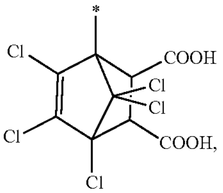
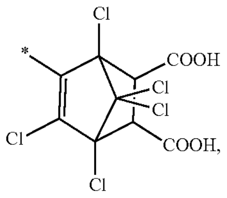
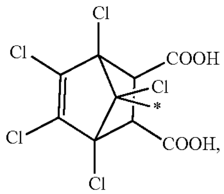
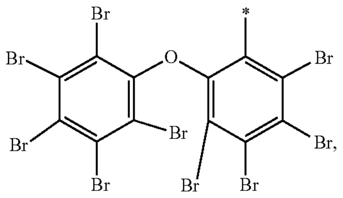
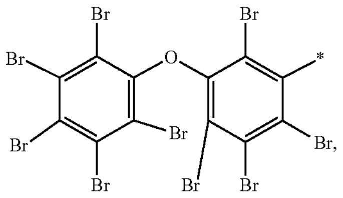
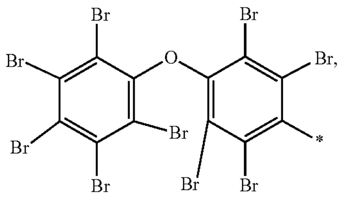
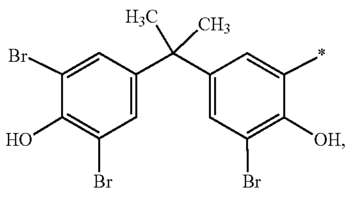
-continued
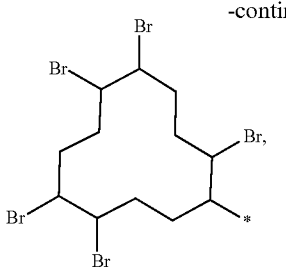
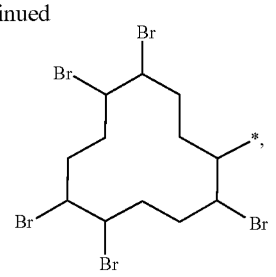
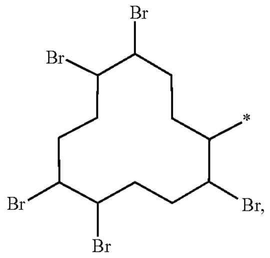
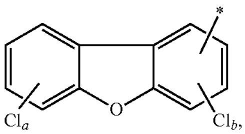
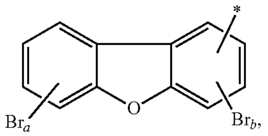
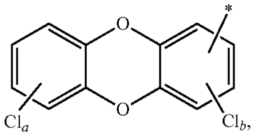
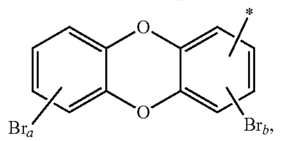
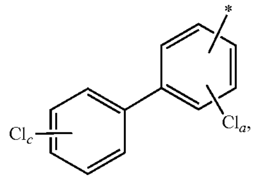 and
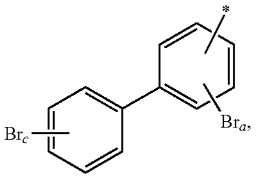
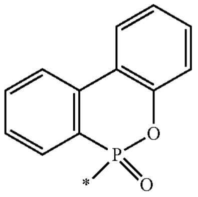, and
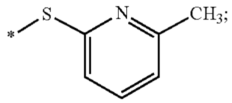
$R^5$ is;
i is 1 to 1,000,000;
j is 1 to 1,000,000;
m is 0 to 32;
s is 0 to 32; and
is a terminal group of the polymer;
=== is a single or a double bond, with only one of === being a double bond.
3. The polymer of claim 2, wherein the polymer has the structure of Formula (Va):

(Va)
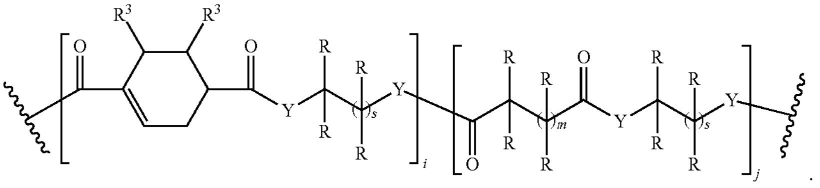
4. The polymer of claim 2, wherein the polymer has the structure of Formula (Vb):
(Vb)
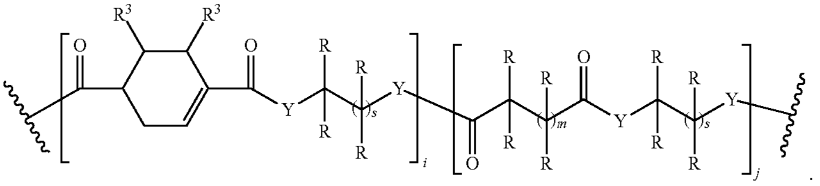
5. The polymer of claim 2, wherein the polymer has the structure of Formula (Vc):
(Vc)
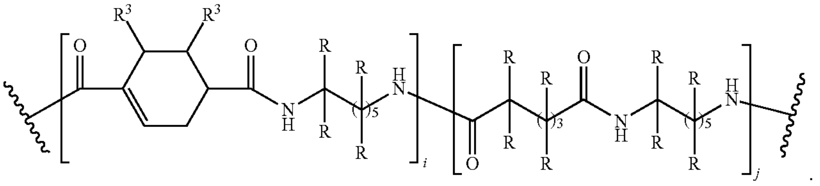
6. The polymer of claim 2, wherein the polymer has the structure of Formula (Vd):
(Vd)
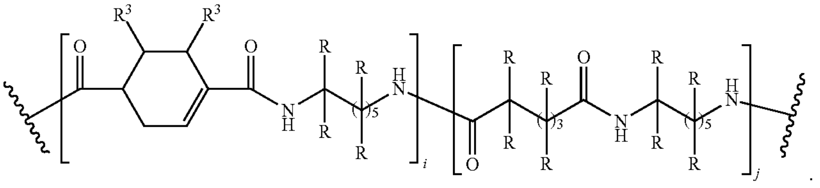
7. The polymer of claim 2, wherein the polymer has the structure of Formula (Vi):

(Vi)
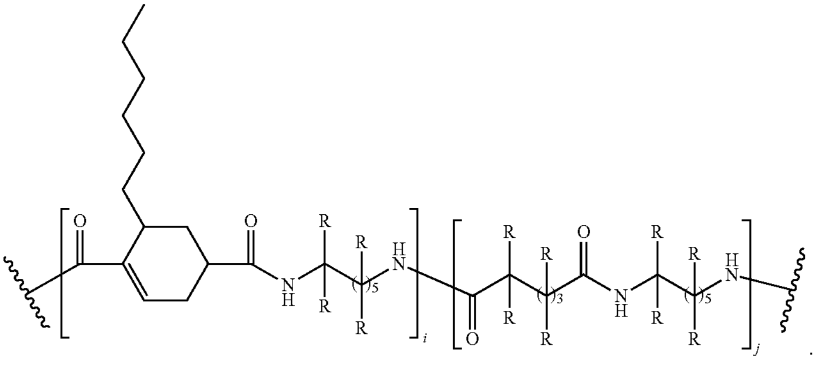
8. The polymer of claim 2, wherein the polymer has the structure of Formula (Vj):
(Vj)
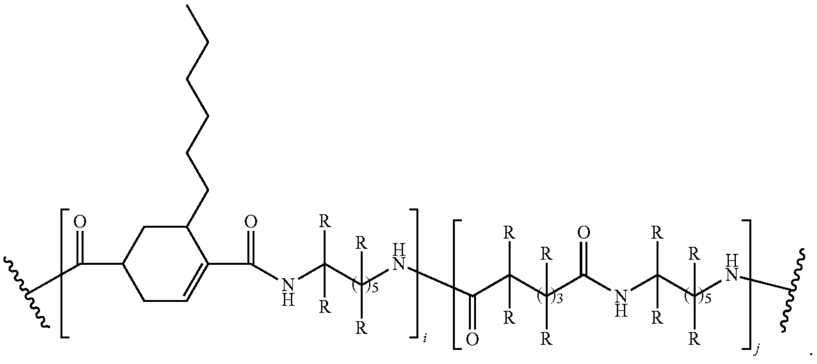
9. The polymer of claim 2, wherein the polymer has the structure of Formula (Vk):
(Vk)
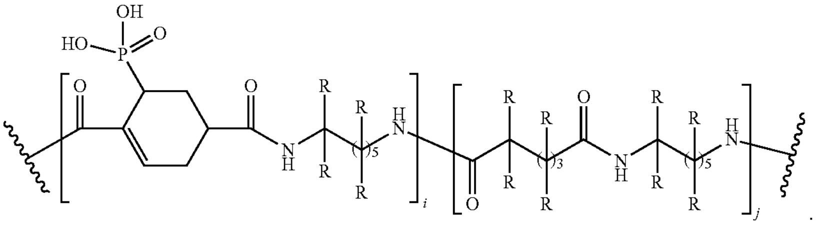
10. The polymer of claim 2, wherein the polymer has the structure of Formula (Vl):
(Vl)
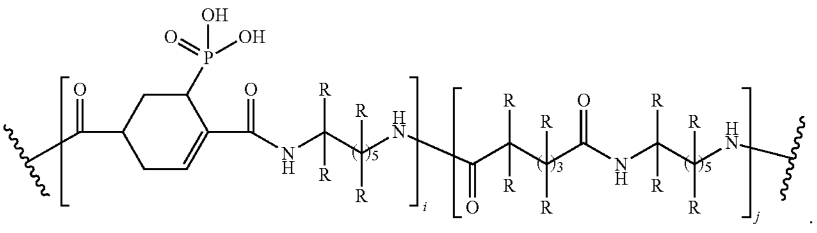

11. The polymer according to claim 2, wherein the polymer is a statistical polymer.

12. The polymer according to claim 2, wherein the polymer is a random polymer.

13. The polymer according to claim 2, wherein the polymer is an alternating polymer.

14. The polymer according to claim 2, wherein the polymer is a block co-polymer.

* * * * *